US009587022B2

(12) United States Patent
Song et al.

(10) Patent No.: US 9,587,022 B2
(45) Date of Patent: Mar. 7, 2017

(54) GLYCAN-MODIFIED ANTI-CD4 ANTIBODY WITH IMPROVED HIV-1 NEUTRALIZING ACTIVITY

(71) Applicant: THE ROCKEFELLER UNIVERSITY, New York, NY (US)

(72) Inventors: Ruijiang Song, Rego Park, NY (US); David D. Ho, Chappaqua, NY (US)

(73) Assignee: THE ROCKEFELLER UNIVERSITY, New York, NY (US)

( * ) Notice: Subject to any disclaimer, the term of this patent is extended or adjusted under 35 U.S.C. 154(b) by 0 days.

(21) Appl. No.: 14/133,256

(22) Filed: Dec. 18, 2013

(65) Prior Publication Data

US 2014/0248295 A1  Sep. 4, 2014

Related U.S. Application Data

(60) Provisional application No. 61/738,777, filed on Dec. 18, 2012.

(51) Int. Cl.
*C07K 16/28* (2006.01)

(52) U.S. Cl.
CPC ...... *C07K 16/2812* (2013.01); *C07K 2317/41* (2013.01); *C07K 2317/76* (2013.01); *C07K 2317/92* (2013.01)

(58) Field of Classification Search
CPC ............ C07K 16/2812; C07K 2317/76; C07K 2317/41
See application file for complete search history.

(56) References Cited

U.S. PATENT DOCUMENTS

| 8,637,024 B2 * | 1/2014 | Ho | ..................... C07K 16/1063 424/136.1 |
| 2006/0269543 A1 | 11/2006 | Chu | |
| 2009/0252724 A1 | 10/2009 | Loetscher et al. | |
| 2012/0121597 A1 | 5/2012 | Ho et al. | |
| 2015/0165022 A1 | 6/2015 | Loetscher et al. | |
| 2015/0166662 A1 | 6/2015 | Song | |

FOREIGN PATENT DOCUMENTS

| EP | 2377886 A1 | 10/2011 |
| WO | WO-2006/125207 A2 | 11/2006 |
| WO | WO-2011/116387 A1 | 9/2011 |

OTHER PUBLICATIONS

Ackerman, M. E., et al., May 2013, Natural variation in Fc glycosylation of HIV-specific antibodies impacts antiviral activity, J. Clin. Invest. 123(5):2183-2192.*
Wright, A. and S. L. Morrison, Jan. 1995, Effect of glycosylation on antibody function: implications for genetic engineering, TIBTECH 15:26-32.*
Wright, A., et al., 1991, Antibody variable region glycosylation: position effects on antigen binding and carbohydrate structure, The EMBO Journal 10(10):2717-2723.*
International Search Report for International Application No. PCT/US2013/076051, mailed Mar. 11, 2014 (5 pages).
Written Opinion of the International Searching Authority for International Application No. PCT/US2013/076051, completed Feb. 21, 2014 (6 pages).
Leung et al., "Engineering a unique glycosylation site for site-specific conjugation of haptens to antibody fragments," J Immunol. 154:5919-26 (1995).
Sharkey et al., "Evaluation of a complementarity-determining region-grafted (humanized) anti-carcinoembryonic antigen monoclonal antibody in preclinical and clinical studies," Cancer Res 55:5935s-45s (1995).
Song et al. "Strategic addition of an N-linked glycan to a monoclonal antibody improves its HIV-1-neutralizing activity," Nat Biotechnol. (Abstract) 31(11):1047-52 (2013).
International Preliminary Report on Patentability for International Patent Application No. PCT/US2013/076051, issued Jun. 23, 2015 (7 pages).
Endo et al., "Glycosylation of the variable region of immunoglobulin G-site specific maturation of the sugar chains," Mol Immunol. 32(13):931-940 (1995).
Gala et al., "V region carbohydrate and antibody expression," J Immunol. 172(9):5489-5494 (2004).
Hurez et al., "Anti-CD4 activity of normal human immunoglobulin G for therapeutic use (intravenous immunoglobulin, IVIg)," Ther Immunol. 1(5):269-277 (1994).
Jacquemin, "Variable region heavy chain glycosylation determines the anticoagulant activity of a factor VIII antibody," Haemophilia. 16(102):16-19 (2010).
Jefferis, "Glycosylation of natural and recombinant antibody molecules," *Glycobiology and Medicine*. John S. Axford, 143-148 (2005).
Mimura et al., "Contrasting glycosylation profiles between Fab and Fc of a human IgG protein studied by electrospray ionization mass spectroscopy," J Immunol Methods. 326(1-2):116-126 (2007).
Non-Final Office Action for U.S. Appl. No. 14/132,667, dated Sep. 16, 2015 (41 pages).
Rudikoff et al., "Single amino acid substitution altering antigen-binding specificity," Proc Natl Acad Sci USA. 79(6):1979-1983 (1982).
Shirai et al., "H3-rules: identification of CDR-H3 structures in antibodies," FEBS Lett. 455(12):188-197 (1999).
Song et al., "Strategic addition of an N-linked glycan to a monoclonal antibody improves it HIV-1-neutralizing activity," Nat Biotechnol. 31(11):1047-1053 (2013).
Response to Non-Final Office Action for U.S. Appl. No. 14/132,667, dated Jan. 15, 2016 (11 pages).
Zheng et al., "The impact of glycosylation on monoclonal antibody conformation and stability," mAbs 3(6): 568-576 (2011).
Extended European Search Report for European Patent Application No. 13866337.2, dated Jul. 12, 2016 (15 pages).
Huang et al., "Impact of variable domain glycosylation on antibody clearance: an LC/MS characterization," Anal Biochem. 349(2):197-207 (2006).

(Continued)

*Primary Examiner* — Jeffrey Parkin
(74) *Attorney, Agent, or Firm* — Clark & Elbing LLP

(57) ABSTRACT

Disclosed herein are glycan-modified anti-CD4 monoclonal antibodies with N-linked glycans attached to the variable region. Expression vectors and cell lines useful for the production of such antibodies, and use of such antibodies for HIV prevention and therapy are also disclosed.

2 Claims, 15 Drawing Sheets

(56) References Cited

OTHER PUBLICATIONS

Jacobson et al., "Safety, pharmacokinetics, and antiretroviral activity of multiple doses of ibalizumab (formerly TNX-355), an anti-CD4 monoclonal antibody, in human immunodeficiency virus type 1-infected adults," Antimicrob Agents Chemother. 53(2):450-7 (2009).
Pace et al., "Anti-CD4 monoclonal antibody ibalizumab exhibits breadth and potency against HIV-1, with natural resistance mediated by the loss of a V5 glycan in envelope," J Acquir Immune Defic Syndr. 62(1):1-9 (2013).
Tachibana et al., "Building high affinity human antibodies by altering the glycosylation on the light chain variable region in N-acetylglucosamine-supplemented hybridoma cultures," Cytotechnology. 23(1-3):151-9 (1997).
Toma et al., "Loss of asparagine-linked glycosylation sites in variable region 5 of human immunodeficiency virus type 1 envelope is associated with resistance to CD4 antibody ibalizumab," J Virol. 85(8):3872-80 (2011).
Wright et al., "Antibody variable region glycosylation: position effects on antigen binding and carbohydrate structure," The EMBO Journal. 10(10):2717-2723 (1991).
Wu et al., "Structure-based engineering of a monoclonal antibody for improved solubility," Protein Eng Des Sel. 23(8):643-51 (2010).
Non-Final Office Action for U.S. Appl. No. 14/132,667, dated May 4, 2016 (15 pages).
Non-Final Office Action for U.S. Appl. No. 14/132,667, dated Jan. 13, 2017.
NCBI Blast Sequence Alignment of SEQ ID Nos: 2, 5 (2017).

* cited by examiner

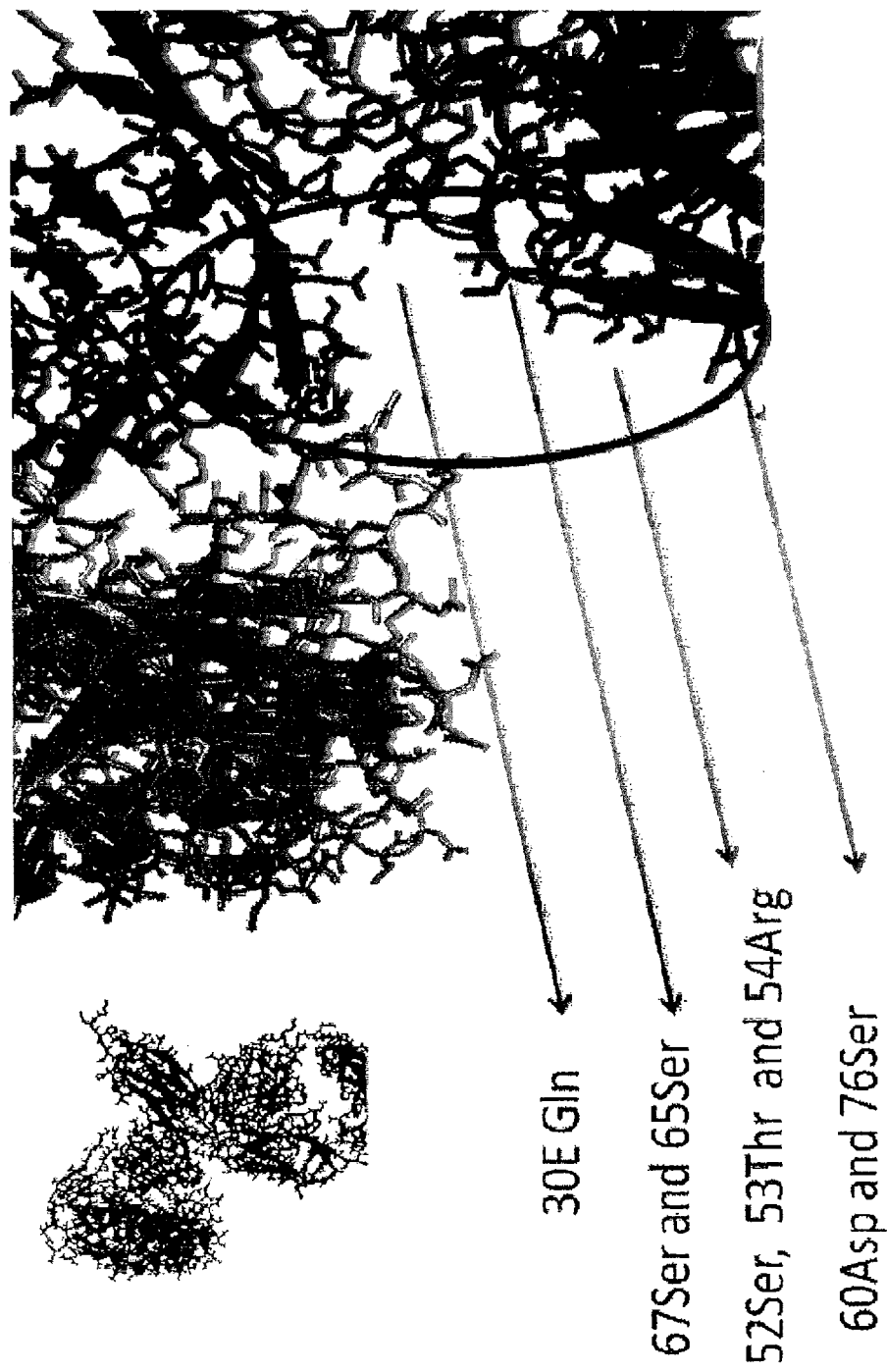

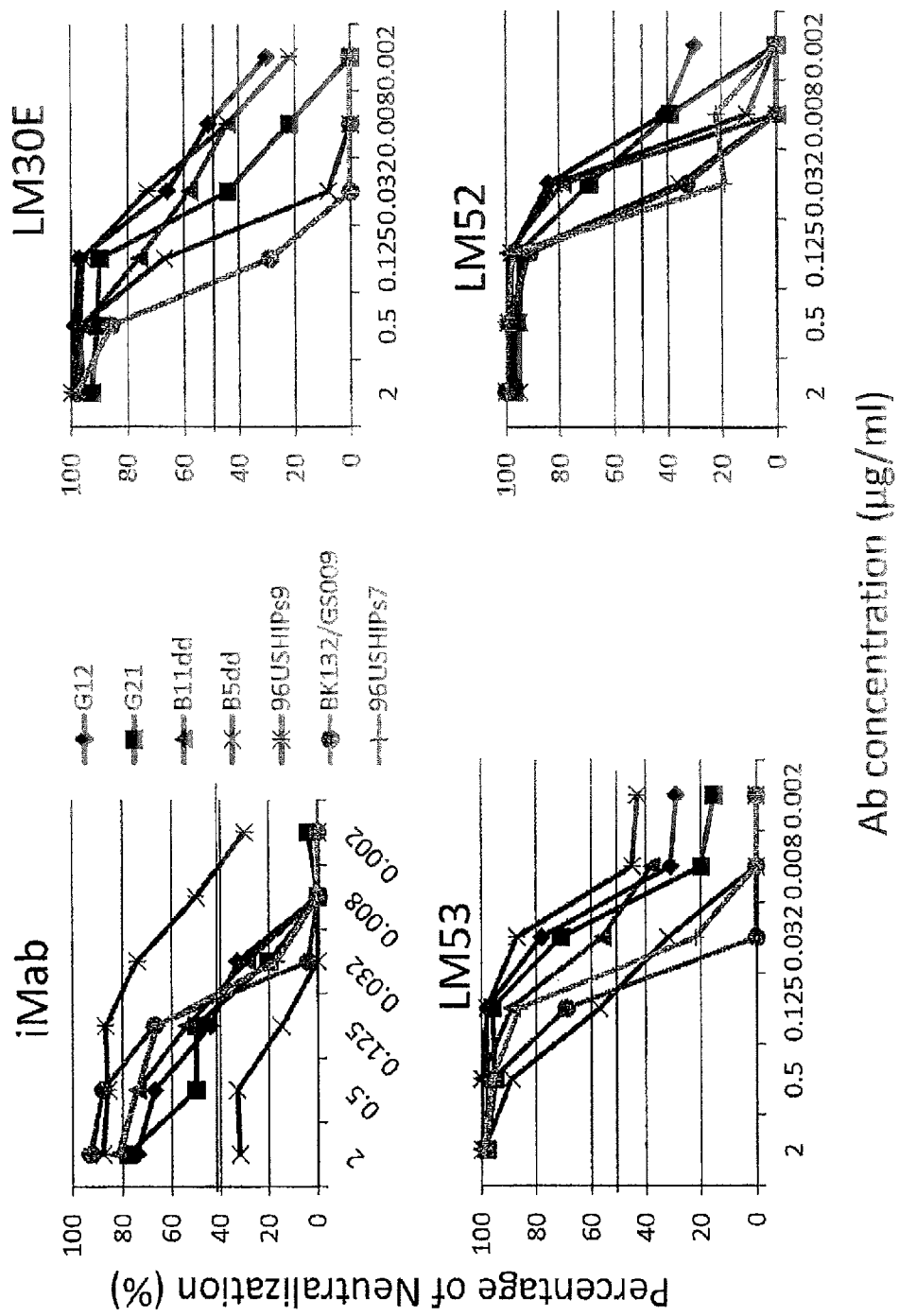

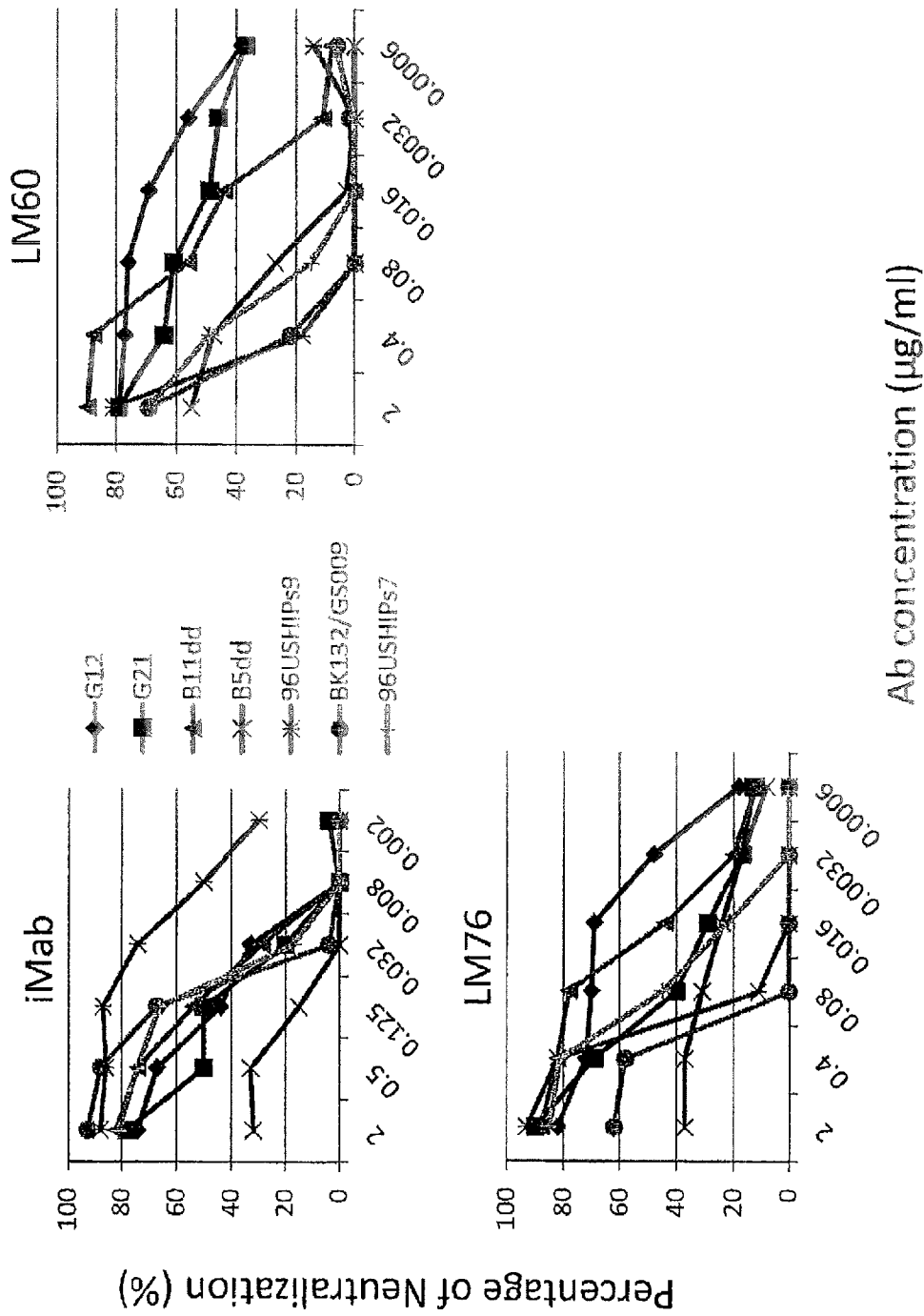

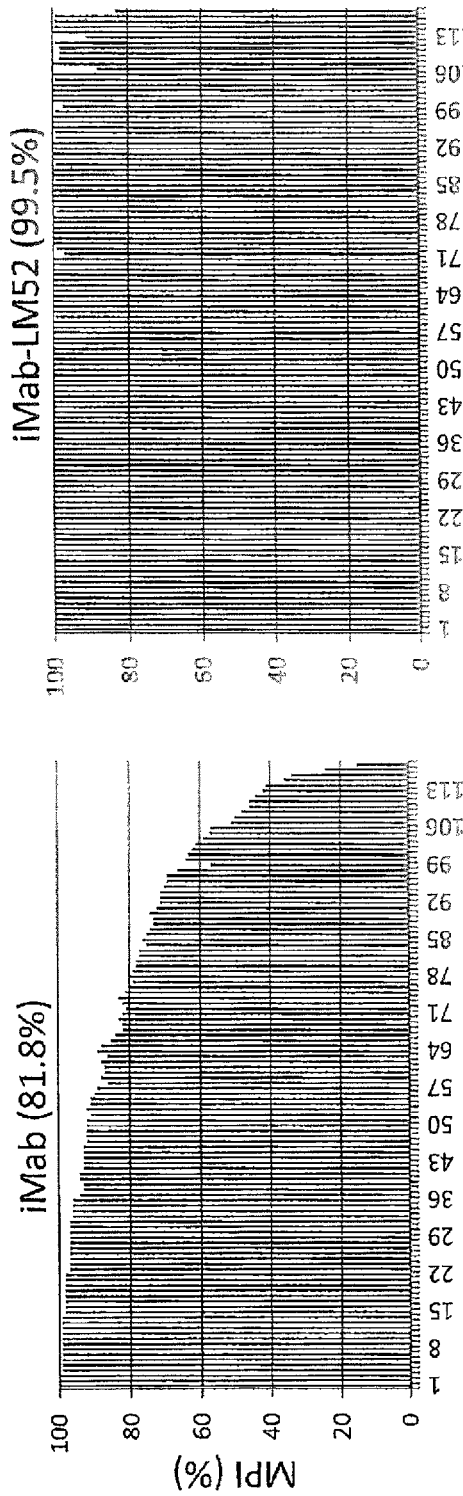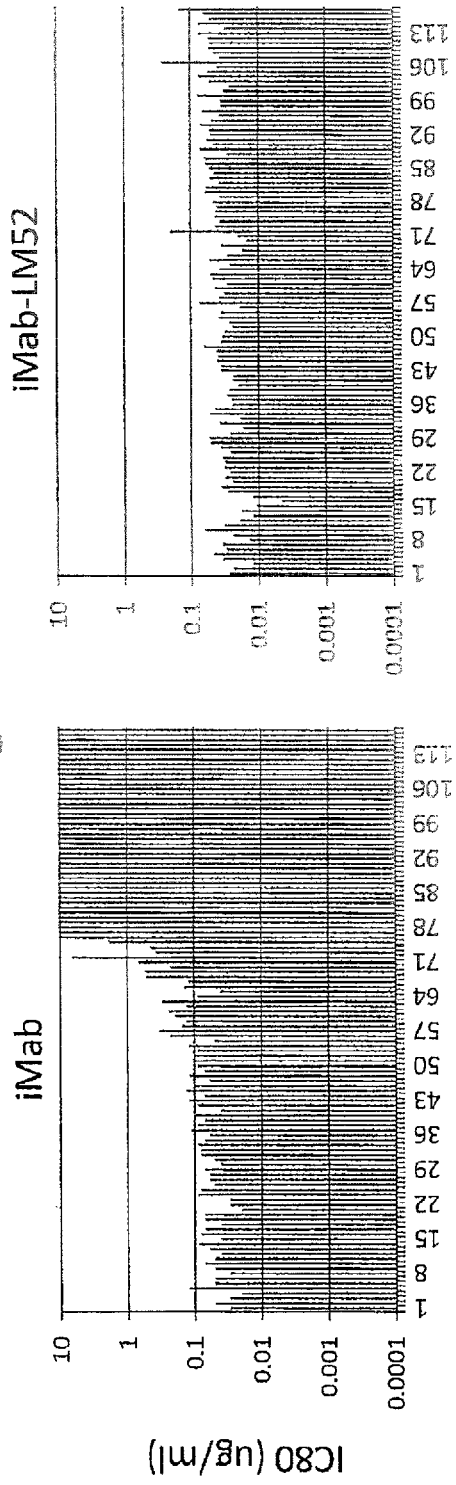
Figure 9A
Figure 9B

SEQUENCE LISTING

<160> NUMBER OF SEQ ID NOS: 4

<210> SEQ ID NO 1
<211> LENGTH: 458
<212> TYPE: PRT
<213> ORGANISM: Homo sapiens

<400> SEQUENCE: 1

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
        355                 360                 365

-continued

```
Gln Cys Leu Leu Ser Asp Ser Gly Gln Val Leu Leu Glu Ser Asn Ile
    370                 375                 380

Lys Val Leu Pro Thr Trp Ser Thr Pro Val Gln Pro Met Ala Leu Ile
385                 390                 395                 400

Val Leu Gly Gly Val Ala Gly Leu Leu Leu Phe Ile Gly Leu Gly Ile
                405                 410                 415

Phe Phe Cys Val Arg Cys Arg His Arg Arg Arg Gln Ala Glu Arg Met
            420                 425                 430

Ser Gln Ile Lys Arg Leu Leu Ser Glu Lys Lys Thr Cys Gln Cys Pro
        435                 440                 445

His Arg Phe Gln Lys Thr Cys Ser Pro Ile
    450                 455

<210> SEQ ID NO 2
<211> LENGTH: 471
<212> TYPE: PRT
<213> ORGANISM: Artificial Sequence
<220> FEATURE:
<223> OTHER INFORMATION: Synthetic or recombinant polypeptide (heavy
      chain of iMab MVI)

<400> SEQUENCE: 2

Met Glu Trp Ser Gly Val Phe Met Phe Leu Leu Ser Val Thr Ala Gly
1               5                   10                  15

Val His Ser Gln Val Gln Leu Gln Gln Ser Gly Pro Glu Val Val Lys
            20                  25                  30

Pro Gly Ala Ser Val Lys Met Ser Cys Lys Ala Ser Gly Tyr Thr Phe
        35                  40                  45

Thr Ser Tyr Val Ile His Trp Val Arg Gln Lys Pro Gly Gln Gly Leu
    50                  55                  60

Asp Trp Ile Gly Tyr Ile Asn Pro Tyr Asn Asp Gly Thr Asp Tyr Asp
65                  70                  75                  80

Glu Lys Phe Lys Gly Lys Ala Thr Leu Thr Ser Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Glu Lys Asp Asn Tyr Ala Thr Gly Ala Trp Phe
        115                 120                 125

Ala Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Phe Glu Gly Gly Pro Ser Val Phe Leu Phe Pro Pro Lys Pro Lys
            260                 265                 270
```

```
Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
                340                 345                 350

Pro Ala Ser Ile Glu Lys Thr Ile Ser Lys Ala Lys Gly Gln Pro Arg
            355                 360                 365

Glu Pro Gln Val Tyr Thr Leu Pro Pro Ser Arg Asp Glu Leu Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
            450                 455                 460

Leu Ser Leu Ser Pro Gly Lys
465                 470

<210> SEQ ID NO 3
<211> LENGTH: 238
<212> TYPE: PRT
<213> ORGANISM: Artificial Sequence
<220> FEATURE:
<223> OTHER INFORMATION: Synthetic or recombinant polypeptide (light
      chain of iMab MVI)

<400> SEQUENCE: 3

Met Glu Trp Ser Gly Val Phe Ile Phe Leu Leu Ser Val Thr Ala Gly
1               5                   10                  15

Val His Ser Asp Ile Val Met Thr Gln Ser Pro Asp Ser Leu Ala Val
            20                  25                  30

Ser Leu Gly Glu Arg Val Thr Met Asn Cys Lys Ser Ser Gln Ser Leu
        35                  40                  45

Leu Tyr Ser Thr Asn Gln Lys Asn Tyr Leu Ala Trp Tyr Gln Gln Lys
50                  55                  60

Pro Gly Gln Ser Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Val Gln Ala Glu Asp Val Ala Val Tyr Tyr
            100                 105                 110

Cys Gln Gln Tyr Tyr Ser Tyr Arg Thr Phe Gly Gly Gly Thr Lys Leu
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160
```

-continued

```
Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 4
<211> LENGTH: 219
<212> TYPE: PRT
<213> ORGANISM: Artificial Sequence
<220> FEATURE:
<223> OTHER INFORMATION: Synthetic or recombinant polypeptide LM52

<400> SEQUENCE: 4

Asp Ile Val Met Thr Gln Ser Pro Asp Ser Leu Ala Val Ser Leu Gly
1               5                   10                  15

Glu Arg Val Thr Met Asn Cys Lys Ser Ser Gln Ser Leu Leu Tyr Ser
            20                  25                  30

Thr Asn Gln Lys Asn Tyr Leu Ala Trp Tyr Gln Gln Lys Pro Gly Gln
        35                  40                  45

Ser Pro Lys Leu Leu Ile Tyr Trp Ala Asn Ser Thr Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ser Tyr Arg Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

GLYCAN-MODIFIED ANTI-CD4 ANTIBODY WITH IMPROVED HIV-1 NEUTRALIZING ACTIVITY

FIELD OF THE DISCLOSURE

This disclosure generally relates to HIV prevention and treatment. This disclosure also generally relates to glycan modification of antibodies. In particular, this disclosure relates to glycan-modified anti-CD4 antibodies useful for HIV prevention and therapy.

BACKGROUND ART

HIV-1 entry is triggered by interaction of the viral envelope (Env) glycoprotein gp120 with domain 1 (D1) of the T-cell receptor CD4. Ibalizumab (iMab) is a potent and broad HIV-1 neutralizing Ab (Jacobson et al., *Antimicrob. Agents Chemother.* 53:450-457, 2009; Kuritzkes et al., *J. Infect. Dis.* 189:286-291, 2004). iMab neutralizes HIV by binding mainly to domain 2 (D2) of the CD4 receptor on host T-cells, thus blocking the ability of HIV to use these CD4 receptors to gain entry into T-cells and produce infection (Burkly et al., *J. Immunol.* 149:1779-178, 1992). In a large panel of primary isolates (118 Env pseudotyped viruses) tested recently, iMab neutralized 92% of all viruses as defined by 50% inhibition of infection, and 47.4% of viruses as defined by 90% inhibition of infection. While iMab can potently inhibit a broad range of HIV isolates, a significant fraction of HIV variants can still escape the inhibitory activity of iMab. It has been reported recently that loss of asparagine-linked glycosylation sites in the variable region 5 of HIV type 1 envelope is associated with resistance to iMab (Toma et al., *J. Virology* 85(8): 3872-2880, 2011; Pace et al., *J. Acquir. Immune Defic. Syndr.* Epub ahead of print: September 2012).

Antibodies are glycosylated at conserved positions in their constant regions, and the presence and structure of the carbohydrate attached to the constant region can affect antibody activity (see review by Wright and Morrison, *TIBTECH* 15: 26-32, 1997).

SUMMARY OF THE DISCLOSURE

This disclosure is directed to enhancing the activity of monoclonal antibodies through glycan modification in the variable region. In various embodiments, this disclosure provides glycan-modified anti-CD4 monoclonal antibodies, expression vectors and cell lines useful for the production of such antibodies, and use of such antibodies for HIV prevention and therapy.

In one embodiment, this disclosure is directed to a glycan-modified anti-CD4 antibody having N-linked glycans attached to the variable region. In some embodiments, the N-linked glycans are attached to the variable domain of the light chain. In other embodiments, the N-linked glycans are attached to the variable domain of the heavy chain. The attachment of glycans is achieved through one or more genetically engineered N-linked glycosylation sites in the variable region.

In one embodiment, the anti-CD4 antibody is a modified form of iMab having an engineered N-linked glycosylation site in its variable region. In some embodiments, the engineered N-linked glycosylation site is located in the variable domain of the light chain of iMab. In other embodiments, the engineered N-linked glycosylation site is located in the variable domain of the heavy chain of iMab. In specific embodiments, the engineered N-linked glycosylation site is located at an amino acid position of the light chain of iMab selected from the group consisting of 30EGln, 52Ser, 53Thr, 54Arg, 65Ser and 67Ser.

In some embodiments, the N-linked glycans attached to the antibody are composed of at least 7 carbohydrate units. In other embodiments, the N-linked glycans are composed of 10-11 carbohydrate units.

In additional embodiments, expression vectors and host cells are provided, which are useful for expressing an anti-CD4 immunoglobulin chain having an engineered N-linked glycosylation site in the variable domain.

In further embodiments, this disclosure provides pharmaceutical compositions containing a glycan-modified anti-CD4 antibody and at least one pharmaceutically acceptable carrier, as well as therapeutic and/or prophylactic methods for treating and/or preventing HIV infection and transmission.

BRIEF DESCRIPTION OF THE DRAWINGS

This patent or application file contains drawings executed in color. Copies of this patent or patent application publication with color drawings will be provided by the Office upon request and payment of the necessary fee.

FIG. 9. A. iMab-LM52 showed improved breadth in a 118 HIV Env-pseudotyped panel as compared to wild type iMab. B. iMab-LM52 showed improved potency (measured by IC80) in a 118 HIV Env-pseudotyped panel as compared to wild type iMab.

DETAILED DESCRIPTION

Figure 1:
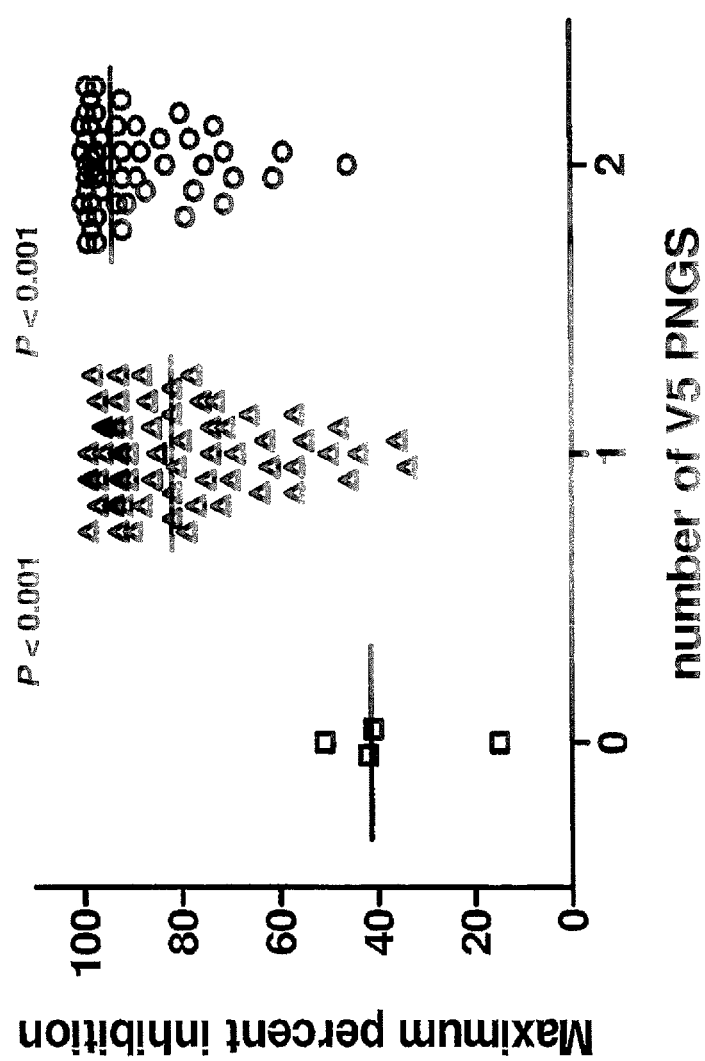
FIG. 1. Number of V5 potential N-linked glycosylation sites (PNGS) is associated with Ibalizumab resistance. Bar indicates median.

This disclosure has demonstrated for the first time that the function of a monoclonal antibody can be improved through glycan modification in the variable region. In particular, it has been discovered by the present inventors that grafting glycans onto the variable region of an anti-CD4 monoclonal antibody can restore a glycan-mediated interaction between the antibody and HIV, such that the antibody with a glycan modification can potently inhibit infection of viral isolates that normally escape the activity of the parent antibody molecule (without the glycan modification). Accordingly, this disclosure provides glycan-modified anti-CD4 monoclonal antibodies, components such as expression vectors and cell lines useful for the production of such antibodies, and use of such antibodies for HIV prevention and therapy.

Definitions

An "antigen" refers to a molecule which contains one or more epitopes and which is capable of eliciting an immunological response. "Antigenic molecules" are also used in a general sense to refer to molecules that are binding targets of the glycan modified proteins disclosed herein.

An "epitope", also known as antigenic determinant, is the portion of an antigenic molecule or molecules that is recognized by the immune system, i.e., B cells, T cells or antibodies. An epitope can be a conformational epitope or a linear epitope. A conformational epitope is formed by discontinuous sections of an antigenic molecule, or formed by multiple molecules. In the case where the antigen is a protein, a conformational epitope can be formed by discontinuous amino acid residues of the same protein molecule, or by amino acid residues on different molecules of the protein (e.g., a quaternary epitope formed by a multimer of the protein). A linear epitope is formed by continuous sections of an antigen, e.g., a continuous sequence of amino acids of a protein antigen.

The term "antibody" is used herein broadly and encompasses intact antibody molecules, which include intact polyclonal, monoclonal, monospecific, polyspecific, chimeric, humanized, human, primatized, single-chain, single-domain, synthetic and recombinant antibodies, and antibody fragments that have a desired activity or function.

The term "antibody fragments", as used herein, includes particularly antigen-binding fragments of an intact antibody. Examples of antigen-binding fragments include, but are not limited to, Fab fragments (consisting of the VL, VH, CL and CH1 domains), Fab' fragments (which differs from Fab fragments by having an additional few residues at the C-terminus of the CH1 domain including one or more cysteines from the antibody hinge region), (Fab')$_2$ fragments (formed by two Fab' fragments linked by a disulphide bridge at the hinge region), Fd fragments (consisting of the VH and CH1 domains), Fv fragments (referring to a dimer of one heavy and one light chain variable domain in tight, non-covalent association which contains a complete antigen recognition and binding site), dAb fragments (consisting of a VH domain), single domain fragments (VH domain, VL domain, VHH domain, or VNAR domain), isolated CDR regions, scFv (or "single chain Fv", referring to a fusion of the VL and VH domains, linked together via a linker), and other antibody fragments that retain antigen-binding function.

The term "variable region" refers to the antigen-binding region of an antibody, which varies greatly between different antibody molecules. The region of an antibody that does not vary the same way and generally engages effector functions of the immune system is called "constant region". Approximately the first 110 amino acids of an immunoglobulin chain (mature form) constitute its variable domain. The two variable domains of the heavy chain (VH) and the two variable domains of the light chain (VL) make up the variable region of an antibody. The six constant domains of the heavy chain (CH$_1$, CH$_2$, and CH$_3$) and the two constant domains of the light chain (CL) make up the constant region of an antibody.

The term "CDR" or "complementarity determining region" refers to the hypervariable regions within the variable domain of an antibody. There are 3 CDRs in each of the heavy chain and light chain variable domains, and are composed of amino acid residues responsible for antigen-binding. The term "framework region" or "FR" refers to the more conserved portions of the variable domains and is composed of residues other than the hypervariable region residues.

The term "antigen-binding site" of an antibody means a conformation and/or configuration formed by amino acids of the antibody to which an antigen binds. For example, the three CDRs of each of the VH and VL domains interact to define an antigen-binding site on the surface of the VH-VL dimer. Together, the six CDRs confer antigen-binding specificity to the antibody. It should be noted, however, a single variable domain (i.e., VH or VL) can also recognize and bind antigen, albeit often less effectively than the whole binding site with all six CDRs.

The term "chimeric antibody" refers to antibodies containing polypeptides from different sources, e.g., different species or different antibody class or subclass. Examples of chimeric antibodies include an antigen-binding portion of a murine monoclonal antibody fused an Fc fragment of a human immunoglobulin. Methods for making chimeric antibodies are known in the art; for example, methods described in patents by U.S. Pat. No. 4,816,397 to Boss et al. and U.S. Pat. No. 4,816,567 to Cabilly et al.

The term "humanized antibody" refers to antibodies that contain non-human sequence elements in a human immunoglobulin backbone or framework. Generally, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having a desired specificity, affinity and capacity. In some instances, framework region (FR) residues of the human immunoglobulin are also replaced by non-human residues. Humanized antibodies may also, in some instances, contain residues that are not found in either the recipient antibody or the donor antibody and introduced to further refine antibody performance. In general, a humanized antibody contains substantially all of at least one, and typically two, variable domains, in which all or substantially all of the hypervariable regions correspond to those of a non-human immunoglobulin and all or substantially all of the framework regions are those of a human immunoglobulin sequence. A humanized antibody optionally also contains at least a portion of an immunoglobulin constant region (Fc), typically that of a human immunoglobulin. Methods for making humanized antibodies are documented in the art; see, for example, by U.S. Pat. No. 5,225,539 to Winter and U.S. Pat. No. 4,816,397 to Boss et al.

The term "non-human primatized antibody" refers to antibodies that contain human sequence elements or non-primate sequence elements in a non-human primate immunoglobulin backbone or framework. For example, non-human primatized antibodies can be made from a non-human primate immunoglobulin (recipient antibody) by replacing residues in a hypervariable region (CDRs) of the recipient antibody with residues from a hypervariable region of a donor antibody from a human or non-primate species such as mouse, rat or rabbit having a desired specificity, affinity and capacity. Alternatively, non-human primatized antibodies can be made suitable for administration to a desirable primate species by using a recipient immunoglobulin having human or non-primate sequences or sequences from a different primate species and introducing the Fc fragment, and/or residues, including particularly framework region residues, from the desirable primate, into the recipient immunoglobulin. Examples of non-human primatized antibodies include "monkeynized" antibodies disclosed herein in the Examples section.

The term "monospecific antibody" refers to antibodies that recognize and bind to one epitope.

The term "polyspecific antibody" refers to antibodies formed from at least two separate antibodies and binding to multiple (i.e., two or more) separate epitopes.

The term "neutralizing antibody" refers to an antibody that inhibits, reduces or completely prevents HIV-1 infection. Whether an antibody is a neutralizing antibody can be determined by in vitro assays described in the Examples section hereinbelow.

The term "potent neutralizing antibody" refers to an antibody which, when used at a low concentration, reduces HIV-1 infection by at least 50%, 60%, 70%, 80%, 90%, 95%, 99% Y or greater. Concentrations below 50 µg/ml, between 1 and 50 µg/ml, or even below 1 g/ml, are considered "low concentrations". In some embodiments, low concentrations are concentrations in the picomolar range, such as 10-900 ng/ml, and include any concentration in that range, such as 800, 700, 600, 500, 400, 300, 200, 100, 75, 50, 25, 10 ng/ml, or even less than 10 ng/ml.

The term "broad neutralizing antibody" refers to an antibody which inhibits HIV-1 infection, as defined by a 50% inhibition of infection in vitro, in more than 50%, 60%, 70%, 80%, 90%, 95%, 99% or greater, of a large panel of (greater than 100) HIV-1 envelope pseudotyped viruses and viral isolates; for example, a large panel of isolates representing envelope diversity by geography, clade, tropism, and stage of infection.

The term "fragment" as used herein refers to a physically contiguous portion of the primary structure of a biomolecule. In the case of proteins, a fragment may be defined by a contiguous portion of the amino acid sequence of a protein and may be at least 3-5 amino acids, at least 6-10 amino acids, at least 11-15 amino acids, at least 16-24 amino acids, at least 25-30 amino acids, at least 30-45 amino acids and up to the full length of the protein minus a few amino acids. In the case of polynucleotides, a fragment is defined by a contiguous portion of the nucleic acid sequence of a polynucleotide and may be at least 9-15 nucleotides, at least 15-30 nucleotides, at least 31-45 nucleotides, at least 46-74 nucleotides, at least 75-90 nucleotides, and at least 90-130 nucleotides. In some embodiments, fragments of biomolecules are immunogenic fragments.

A "fusion protein" refers to two or more peptides of different origins connected to each other via a linker or linkers. For example, a fusion protein can include a protein conjugated to an antibody. Other examples include, an antibody conjugated to a different antibody or an antibody conjugated to a Fab fragment. The Fab fragment can be conjugated to the N terminus or C terminus of the heavy or light chain of the antibody, or other regions within the antibody.

A "peptide" is any compound formed by the linkage of two or more amino acids by amide (peptide) bonds, usually a polymer of alpha-amino acids in which the alpha-amino group of each amino acid residue (except the NH2 terminus) is linked to the alpha-carboxyl group of the next residue in a linear chain. The terms peptide, polypeptide and poly (amino acid) are used synonymously herein to refer to this class of compounds without restriction as to size, unless indicated to the contrary. Members of this class having a large size are also referred to as proteins and include antibodies.

Glycan-Modified Anti-CD4 Monoclonal Antibodies

This glycan modification approach disclosed herein is applicable to anti-CD4 monoclonal antibodies, which can be a monoclonal antibody that is a monospecific, polyspecific, chimeric, humanized, human, non-human primatized, single-chain, and/or single-domain antibody. The present approach is also applicable to fragments of anti-CD4 monoclonal antibodies, especially antigen-binding fragments of anti-CD4 monoclonal antibodies.

Anti-CD4 antibodies have been described in the art and can also be readily generated as the protein sequence of the CD4 receptor is available to those skilled in the art. CD4 has four immunoglobulin domains (D1 to D4) that are located on the extracellular surface of the cell, and uses its D1 domain to interact with the $\beta_2$-domain of MHC class II molecules. In some embodiments, the anti-CD4 antibody binds to one or more of D1, D1-D2 junction, D2, the BC or FG loop of D2, or any combination thereof. In specific embodiments, anti-CD4 antibodies used in this disclosure are directed principally to the second immunoglobulin-like domain (D2) (amino acid positions 98-180) of the CD4 receptor. Antibodies directed to the D2 domain of CD4 have the desirable property of blocking HIV infection without interfering with immune functions mediated by interaction of CD4 with the major histocompatibility complex (MHC) class II molecules. In other embodiments, the anti-CD4 antibody used in this disclosure binds to an epitope located in the BC-loop of D2 near the D1-D2 junction of the CD4 receptor (amino acids 121-127). In still other embodiments, the anti-CD4 antibody binds to the FG-loop of D2 (amino acids 163-165) and part of D1 (amino acids 77-96). The amino acid numbering corresponds to positions of the mature form of the CD4 receptor, not including the signal peptide. The amino acid sequence of the human CD4 receptor is set forth in SEQ ID NO: 1, in which amino acids 1-25 represent a signal peptide, amino acids 26-122 constitute D1, and amino acids 123-205 constitute D2.

In a specific embodiment, the anti-CD4 monoclonal antibody is the humanized antibody, Ibalizumab or "iMab" (previously known as TNX-355, or hu5A8). iMab potently blocks infection by a broad spectrum of HIV-1 isolates and targets an epitope located in the BC-loop of D2 near the D1-D2 junction of the CD4 receptor, without interfering with immune functions mediated by interaction of CD4 with the major histocompatibility complex (MHC) class II molecules. The amino acid sequences for the heavy chain and light chain of a derivative IgG1 version of iMab called MV1 iMab are set forth in SEQ ID NOS: 2-3, respectively.

Glycan modification disclosed herein involves adding glycans to an engineered N-linked glycosylation site within the variable region of an anti-CD4 antibody. In eukaryotic cells, glycans are attached to asparagine residues within the consensus sequence Asn-X-Ser/Thr of newly synthesized polypeptides as they emerge from the ribosome. This N-linked glycosylation process is an enzyme-directed process which occurs in the ER and the Golgi apparatus. For purposes of this disclosure, the Asn residue within a consensus sequence Asn-X-Ser/Thr is referred to as the "N-linked glycosylation site". The skilled artisan can employ a variety of molecular cloning techniques to engineer an N-linked glycosylation site within the variable region of an anti-CD4 monoclonal antibody, which may include one or more insertions, deletions and/or substitutions of amino acids in order to obtain a consensus N-linked glycosylation sequence Asn-X-Ser/Thr.

In some embodiments, an N-linked glycosylation site is engineered within the V-domain of the light chain (VL) of an anti-CD4 monoclonal antibody. In other embodiments, an N-linked glycosylation site is engineered within the V-domain of the heavy chain (VH) of an anti-CD4 monoclonal antibody. One may consider conducting a 3-D modeling analysis of the relevant antibodies, the CD4 receptor and the HIV gp120 protein to facilitate a determination of a suitable or a more desirable location within the antibody for an N-linked glycosylation site. As illustrated, this disclosure demonstrates that for iMab, an N-linked glycosylation site can be introduced to a location that is close to the V5 loop of the HIV gp120 protein in a 3-D modeling analysis.

In some embodiments, an N-linked glycosylation site is engineered at an amino acid position of the light chain of iMab selected from positions 30E Gln, 52Ser, 53Thr, 54Arg, 65Ser and 67Ser. The numbering of these positions is based on the mature form of the light chain (devoid of the first 16 amino acid signal sequence). In specific embodiments, the N-linked glycosylation site is engineered at one of 30E Gln, 52Ser, or 53Thr of the iMab light chain. In a particular embodiment, the N-linked glycosylation site is engineered at position 52Ser. An example of such a modified iMab light chain having an engineered N-linked glycosylation site at position 52 is listed in SEQ ID NO: 4.

Once an N-linked glycosylation site has been engineered within the variable region of an anti-CD4 monoclonal antibody, glycan-modified forms of such antibody can be readily produced using suitable recombinant expression systems. For example, a cell line suitable for recombinant expression of antibody molecules and capable of N-linked glycosylation can be transfected with expression vector(s) encoding the heavy chain and light chain of an anti-CD4 antibody, wherein at least a variable domain of the heavy chain or light chain has been engineered to include an N-linked glycosylation site. Antibody-containing culture supernatants can be collected and subjected to any appropriate chromatography to obtain a substantially purified antibody preparation.

Cell lines suitable for recombinant expression of antibody molecules are readily available to those skilled in the art, and are generally capable of N-linked glycosylation. In eukaryotes, the N-linked glycosylation process occurs co-translationally and the initial step takes place at the luminal side of the ER membrane, involving the transfer of a $Glc_3Man_9GlcNAc_2$ oligosaccharide to nascent polypeptide chains. This precursor structure is then further modified by a series of glycosidases and glycosyltransferases. Following the removal of the three glucose residues by glucosidase I and II, one specific terminal α-1,2-mannose is removed by mannosidase I. These reactions are well conserved between most lower and higher eukaryotes. At this point, correctly folded $Man_8GlcNAc_2$ N-linked glycosylated proteins may exit the glycosylation machinery; alternatively, they may continue and undergo further species- and cell type-specific processing, catalyzed by a series of enzymes, to produce hybrid and/or complex type glycans. See FIG. 7A. See also review by Wright and Morrison, *TIBTECH* 15: 26-32 (1997); U.S. Pat. Nos. 6,602,684; and 7,029,872, for example. In higher eukaryotes, the $Man_8GlcNAc_2$ structures are further trimmed by several α-1,2-mannosidases. The resulting $Man_5GlcNAc_2$ N-linked glycans are subsequently modified by the addition of a β-1,2-linked GlcNAc residue in a reaction catalyzed by GlcNAc transferase I (GnT-I), the resulting $GlcNAcM_8GlcNAc_2$ structure leading ultimately to the formation of "hybrid-type" N-linked glycans. Alternatively, the $GlcNAcM_8GlcNAc_2$ structure is acted on by mannosidase II (Man-II) to move two mannoses, and then by GnT-II to add a second β-1,2-GlcNAc. Glycans with the resulting structure in which both core-α-mannose residues are modified by at least one GlcNAc residue, are called "complex type" N-linked glycans. Additional branching can be initiated by GnT-IV, GnT-V, and GnT-VIs. Galactose and sialic acid residues are further added by galactosyltransferases and sialyltransferases, respectively.

According to this invention, the N-linked glycans added to the variable region of an anti-CD4 antibody should include at least 7, 8, 9, 10, 11 or 12 carbohydrate units or "rings". The term "carbohydrate units" refers to individual saccharide molecules that are linked to each other to make up the native N-glycans in eukaryotic cells; i.e., they include glucose, mannose, N-acetylglucosamine, galactose, and sialic acid. The precise structure (i.e., the compositions and serial linkage) of the N-glycans on an antibody may not be entirely critical as long as the N-glycans include at least 7 units. Examples of N-linked glycans include those typically seen in mammalian cells, e.g., $Man_8GlcNAc_2$ (the GlcNAc at the end being linked to Asn), $Man_5GlcNAc_2$, $GlcNAcMan_5GlcNAc_2$, $GlcNAc_2Man_3GlcNAc_2$, $Gal_2GlcNAc_2Man_3GlcNAc_2$, (sialic acid)$_2GlcNAc_2Man_3GlcNAc_2$, $GalGlcNAcMan_5GlcNAc_2$, as well as the bisected bi-antennary complex, the tri-antennary complex, tri'-antennary complex and tetra-antennary complex N-glycans described in U.S. Pat. No. 6,602,684 (e.g., FIG. 1 therein), incorporated herein by reference.

According to this invention, suitable cells lines for recombinant expression of glycan-modified antibodies are eukaryotic cells, including especially mammalian cell lines such as Chinese hamster ovary (CHO) cells, Baby Hamster Kidney (BHK) cells, (Murine myeloma) NS0 cells, Murine myeloma SP2/0 cells, human embryonic kidney 293 (HEK293 or 293) cells, mouse embryonic fibroblast 3T3 cells, and cell lines derived therefrom as long as the derived cells can effectively express a recombinant antibody with N-linked glycosylation. Many of these cells are available through American Tissue Culture Collection (ATCC) or commercial sources. Genetically modified cells that produce glycoproteins having altered glycoforms, e.g., glycoproteins having a particular class of N-linked glycans (such as bi-antennary complex N-linked oligosaccharides) modified with bisecting N-acetylglucosamine (GlcNAc), as described in U.S. Pat. No. 6,602,684, incorporated herein by reference), can also be employed to produce the antibodies of this invention. Other eukaryotic cells which may be appropriate include insect cells and yeast cells, such as baker yeast *S. cerevisiae* and methylotrophic yeast such as *Pichia pastoris*, including particularly yeast strains genetically modified to produce proteins having human N-glycan forms. See, e.g., U.S. Pat. Nos. 7,029,872, and 7,449,308, both incorporated herein by reference.

One can confirm that N-linked glycans are attached to an antibody molecule produced from cells by treating the antibody molecule isolated from cell culture with enzymes (e.g., PNGase). A shift in the apparent molecular weight of the antibody (which can be detected in SDS-PAGE, Western blot, and the like) as a result of the treatment indicates that N-linked glycans are indeed attached to the antibody molecule. The size of the N-linked glycans can be estimated by comparing with N-linked glycans of known sizes. For a more detailed analysis, the N-linked glycans attached to the antibody can be analyzed by DNA sequencer assisted (DSA), fluorophore assisted carbohydrate electrophoresis (FACE), or MALDI-TOF MS, for example, all of which are techniques well documented in the art. For example, in a DSA-FACE analysis, N-linked glycans are released from a glycosylated antibody peptide: N-glycosidase F (PNGase F). The released N-linked glycans are then derivatized with the fluorophore 8-aminopyrene-1,3,6-trisulfonate (APTS) by reductive amination. After removal of excess APTS, the labeled N-linked glycans are analyzed with an ABI 3130 DNA sequencer. See, e.g., Laroy et al. (*Nat. Protoc.* 1: 397-405 (2006)). See also U.S. Pat. No. 6,602,684 for MALDI-TOF MS analysis of N-linked glycans on recombinantly produced proteins.

Glycan-modified antibodies can be evaluated in various functional assays to confirm their effectiveness in neutralizing HIV, including assays to determine the breadth and potency of the antibodies against large panels of viral isolates as described in the examples section.

Figure 7A:
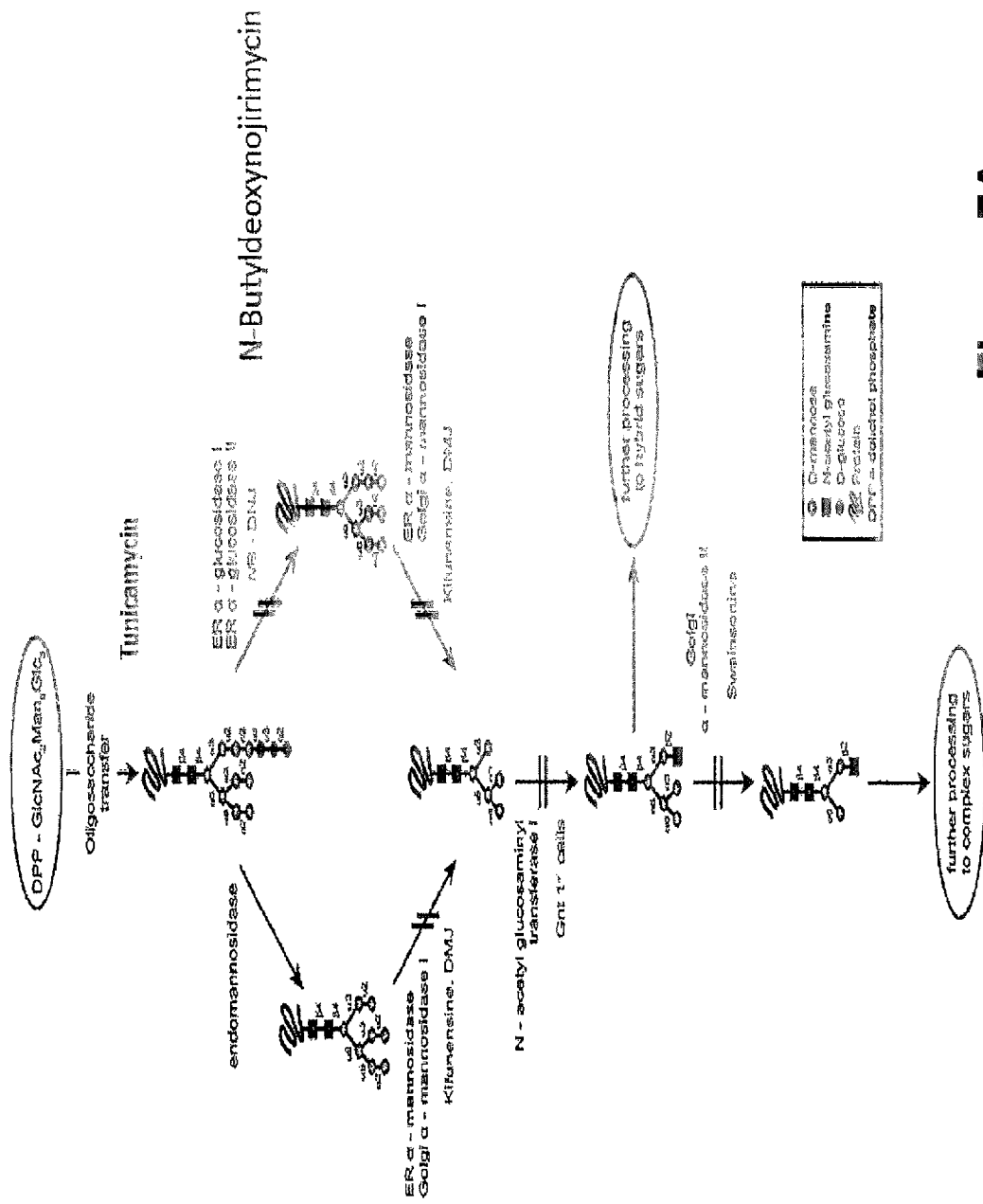
FIG. 7. A. Natural cellular glycosylation pathway and inhibitors and mutant cell line used for generation of iMab light chain mutant LM52 with glycans of different sizes (adapted from *J Virol.* 2010 October; 84(20): 10510-10521, with modifications). B. LM52 mutant was produced in 293A cells or 293 Gnt $1^{-/-}$ cells with or without tunicamycin or Kifunensine to generate mutants with different sized glycans in the ibalizumab light chain. C. Analysis of the N-linked glycans of LM52 by mass spectrometry. D. A positive correlation was observed between the size of the glycan and the neutralization activity.

In some embodiments of this invention, it may be desirable to produce antibodies with substantially homogeneous N-linked glycans or one class of N-linked glycans. By "substantially homogeneous" it is meant that at least 50%, 60%, 75%, 80%, 85%, 90% or even 95% of the N-linked glycans on the antibody molecules in a preparation are of the same structure, same size (i.e., same molecular weight, or alternatively, same number of carbohydrate "rings"), or same range of size (e.g., 9-12 "rings", or 10-11 "rings"), and/or type. This can be achieved by utilizing cell lines genetically engineered to express or overexpress a selected set of enzymes involved in N-glycosylation (see, e.g., U.S. Pat. Nos. 6,602,684 and 7,029,872), or to disrupt an enzyme at an intermediate stage in the N-glycosylation pathway (e.g., GnT1 knockout strains as depicted in FIG. 7A), or to utilize one or more inhibitors that target specific processing enzymes, or a combination thereof. Examples of inhibitors include Kifunensine, DMJ (for "deoxymannojirimycin"), and Swainsonine (see FIG. 7A).

Pharmaceutical Formulations

Pharmaceutical formulations containing a glycan-modified antibody disclosed herein can be prepared by mixing the antibody with optional pharmaceutically acceptable carriers. Pharmaceutically acceptable carriers include solvents, dispersion media, isotonic agents and the like. The carrier can be liquid, semi-solid, e.g. pastes, or solid carriers. Examples of carriers include water, saline solutions or other buffers (such as phosphate, citrate buffers), oil, alcohol, proteins (such as serum albumin, gelatin), carbohydrates (such as monosaccharides, disaccharides, and other carbohydrates including glucose, sucrose, trehalose, mannose, mannitol, sorbitol or dextrins), gel, lipids, liposomes, resins, porous matrices, binders, fillers, coatings, stabilizers, preservatives, antioxidants including ascorbic acid and methionine, chelating agents such as EDTA; salt forming counter-ions such as sodium; non-ionic surfactants such as TWEEN™, PLURONICS™ or polyethylene glycol (PEG), or combinations thereof.

The formulation can contain more than one active compound, e.g., one or more antibodies, in combination with one or more additional beneficial compound for preventing and treating HIV infections.

The active ingredients can be combined with the carrier in any convenient and practical manner, e.g., by admixture, solution, suspension, emulsification, encapsulation, absorption and the like, and can be made in formulations such as tablets, capsules, powder (including lyophilized powder), syrup, suspensions that are suitable for injections, ingestions, infusion, or the like. Sustained-release preparations can also be prepared.

Methods of Treatment and Prevention

In a further aspect, the glycan modified antibodies disclosed herein, optionally provided in pharmaceutically acceptable carrier, are employed for the treatment and prevention of HIV infection in a subject, as well as prevention of HIV transmission.

The term "treatment" of HIV infection refers to effective inhibition of the HIV infection so as to delay the onset, slow down the progression, reduce viral load, and/or ameliorate the symptoms caused by HIV infection.

The term "prevention" of HIV infection means the onset of HIV infection is delayed, and/or the incidence or likelihood of HIV infection is reduced or eliminated.

The term "prevention" of HIV transmission means the incidence or likelihood of HIV being transmitted from one individual to another (e.g., from an HIV-positive woman to the child during pregnancy, labor or delivery, or breastfeeding; or from an HIV-positive subject to an HIV-negative partner) is reduced or eliminated.

The term "subject" refers to any primate subject, including human and non-human subjects (e.g., rhesus subjects).

To treat and/or prevent HIV infection, a therapeutic amount of a glycan-modified antibody disclosed herein is administered to a subject in need.

The term "therapeutically effective amount" means the dose required to effect an inhibition of HIV infection so as to treat and/or prevent HIV infection. The dosage of an antibody depends on the disease state and other clinical factors, such as weight and condition of the subject, the subject's response to the therapy, the type of formulations and the route of administration. The precise dosage to be therapeutically effective and non-detrimental can be determined by those skilled in the art. As a general rule, a suitable dose of an antibody for the administration to adult humans parenterally is in the range of about 0.1 to 20 mg/kg of patient body weight per day, once a week, or even once a month, with the typical initial range used being in the range of about 2 to 10 mg/kg. Since the antibodies will eventually be cleared from the bloodstream, re-administration may be required. Alternatively, implantation or injection of antibodies provided in a controlled release matrix can be employed.

The antibodies can be administered to the subject by standard routes, including the oral, transdermal or parenteral (e.g., intravenous, intraperitoneal, intradermal, subcutaneous or intramuscular). In addition, the antibodies can be introduced into the body, by injection or by surgical implantation or attachment such that a significant amount of a desirable antibody is able to enter blood stream in a controlled release fashion.

The description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein.

The present description is further illustrated by the following examples, which should not be construed as limiting in any way. The contents of all cited references (including literature references, issued patents, and published patent applications as cited throughout this application) are hereby expressly incorporated by reference.

EXAMPLE 1

Cell lines, reagents, and pseudotyped viruses. TZM-bl cells (catalog no. 8129) were obtained from the NIH ARRRP. This is a genetically engineered HeLa cell line that expresses CD4, CXCR4, and CCR5 and contains Tat-responsive reporter genes for firefly luciferase and *Escherichia coli* β-galactosidase under regulatory control of an HIV-1 long terminal repeat. The Standard Reference Panels of Subtype B HIV-1 Env clones from acute and early infections and Env-deficient backbone plasmid (SG3ΔEnv) were also obtained through the NIH ARRRP (Li et al., 2005). The 118 virus panel used in the experiments described in Examples 2-3 and FIG. 9 contained viruses from a number of different subtypes, clades, circulating recombinant forms, tropisms, and stages of infection (see Seaman et al., *J Virol* 84:1439-52, 2009). HIV-1 env pseudotyped viruses were prepared by co-transfection of 293A cells (Invitrogen) with an Env-expression plasmid and SG3ΔEnv. Recombinant sCD4 comprising the full-length extracellular domain of human CD4 was obtained from Progenics Pharmaceuticals, Inc. (Tarrytown, N.Y.). Ibalizumab protein was provided by TaiMed Biologics (Irvine, Calif.). Plasmids pMV1 and pLC, which encode for ibalizumab heavy chain and light chain, respectively, were amplified from cDNA and cloned into pcDNA3.1 (+) (Invitrogen). N-Acetylglucosaminyltransferase I-negative GnT1(−) human embryonic kidney (HEK) 293S cells limit the N-linked glycosylation of expressed proteins were from ATCC.

Addition of N-Linked Glycosylation Sites in the Ibalizumab Light Chain. The NXS/T sequence was introduced in the light chain of ibalizumab to create ibalizumab light chain mutants (LM). Mutagenesis was carried out with Quikchange mutagenesis kit (Stratagene, Santa Clara, Va.). Ibalizumab LM constructs were sequenced and transiently transfected into HEK293A cells using a 1:1 ratio of heavy and light chain plasmids with polyethylenimine (PEI)-DNA complex. Supernatants were harvested on day 5 post transfection and ibalizumab LM proteins were purified with a protein A agarose (Thermo Scientific, Rockford, Ill.) column. Ibalizumab and its LMs 30E, 52, and 53 were treated with PNGase F (New England Biolabs, Ipswich, Mass.) under denaturing conditions. Ibalizumab and the LMs before and post treatment were then analyzed by SDS-PAGE.

Virus Neutralization Assay Using TZM-bl Cells. Neutralization assay was performed based on Wei et al. (25) with modification. Briefly, 10,000 cells per well were seeded in a 96-well plate in 100 µl/well DMEM supplemented with 10% fetal bovine serum (D10) and incubated overnight at 37° C. The next day, 100 µl of serial diluted ibalizumab or LM proteins were added to the cells and incubated for 1 hour at 37° C. Then, 50 µl/well of 200 50%-tissue-culture-infective-doses ($TCID_{50}$) of replication competent or pseudotyped HIV-1 virus were prepared in D10 containing DEAE-Dextran (Sigma, St. Louis, Mo.) and added to the cells. The cells were incubated for 48 hours at 37° C. and the β-galactosidase activity was measured using the Galacto-Star System (Applied Biosystems, Cedarville, Ohio). The percentage of inhibition on viral infectivity was calculated as 1 minus the ratio of antibody-treated wells versus untreated-infected wells multiplied by 100. The $IC_{50}$ and $IC_{80}$ values (the antibody concentrations that confer 50% and 80% neutralization, respectively) were calculated by a non-linear regression analysis.

Biacore Assay. Binding affinity analyses were performed with a T3000 instrument (GE Healthcare, Piscataway, N.J.). Immobilization of ibalizumab or LMs to CM5 sensor chips was performed following the standard amine coupling procedure. Briefly, carboxyl groups on the sensor chip surface were activated by injection of a solution containing 0.2 M EDC and 0.05 M NHS. Next, sCD4 protein in 10 mM NaOAc buffer (pH5) was flowed over the chip surface until the desired level of response units was achieved. After unreacted protein was washed out, excess active ester groups on the sensor surface were capped by the injection of 1 M ethanolamine, pH 8.0. Binding experiments were performed at 25° C. in HBS-EP buffer (GE Healthcare). Binding kinetics were measured by passing various concentrations of human sCD4 protein over the chip surface. For kinetics data analysis, the kinetic parameters (km, association rate constant; $k_{off}$, dissociation rate constant; $K_D$, equilibrium dissociation constant) were determined by collectively fitting the overlaid sensograms using the BIAevaluation 4.1 software.

EXAMPLE 2

Sequence analysis of a panel of 118 viral isolates suggests that ibalizumab resistance was associated with the number of potential N-linked glycosylation sites (PNGS) in the V5 loop of gp120 (Pace et al., *J. Acquir. Immune Defic. Syndr.* Epub ahead of print: September 2012). As shown in FIG. 1, viruses having two N-linked glycosylation sites in V5 were sensitive to ibalizumab, whereas viruses having no N-linked glycosylation site in V5 were resistant. Bar indicates median. Interestingly, clinical viral isolates that have developed resistance to ibalizumab monotherapy also display a loss in a potential V5 glycosylation site (Toma et al., *J Virology* 85(8): 3872-2880, 2011).

Figure 2:
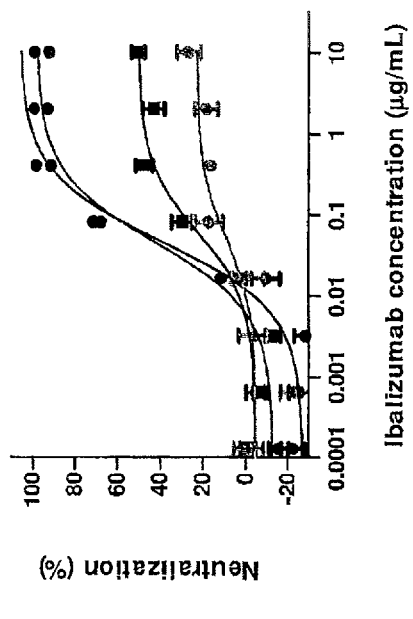
FIG. 2. Loss of V5 N-terminal PNGS confers HIV resistance to ibalizumab.

One wild-type virus (AC10.0.29) in the panel has two N-linked glycosylation sites in V5 and is naturally sensitive to ibalizumab. The V5 N-linked glycosylation sites in this virus were systematically deleted using site-directed mutagenesis, and the resulting mutant viruses became resistant to ibalizumab (FIG. 2).

Figure 3:
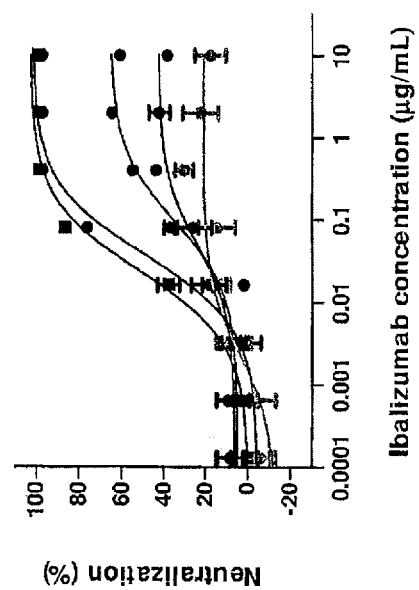
FIG. 3. Introduction of a V5 N-terminal PNGS confers HIV sensitivity to ibalizumab.

Another wild-type virus (RHPA4259.7) in the panel has no N-linked glycosylation site in V5 and is naturally resistant to ibalizumab. This virus was modified to systematically add N-linked glycosylation sites in V5. As shown in FIG. 3, the resulting mutant viruses became sensitive to ibalizumab.

EXAMPLE 3

Analysis of superimposed crystal structures of ibalizumab, CD4 and HIV gp120 revealed that the V5 loop of gp120 is adjacent to the interaction site between the light chain of ibalizumab and CD4. Additional modeling analysis suggested that ibalizumab may normally inhibit HIV through steric hindrance, and that loss of a glycan on gp120

Figure 6B:
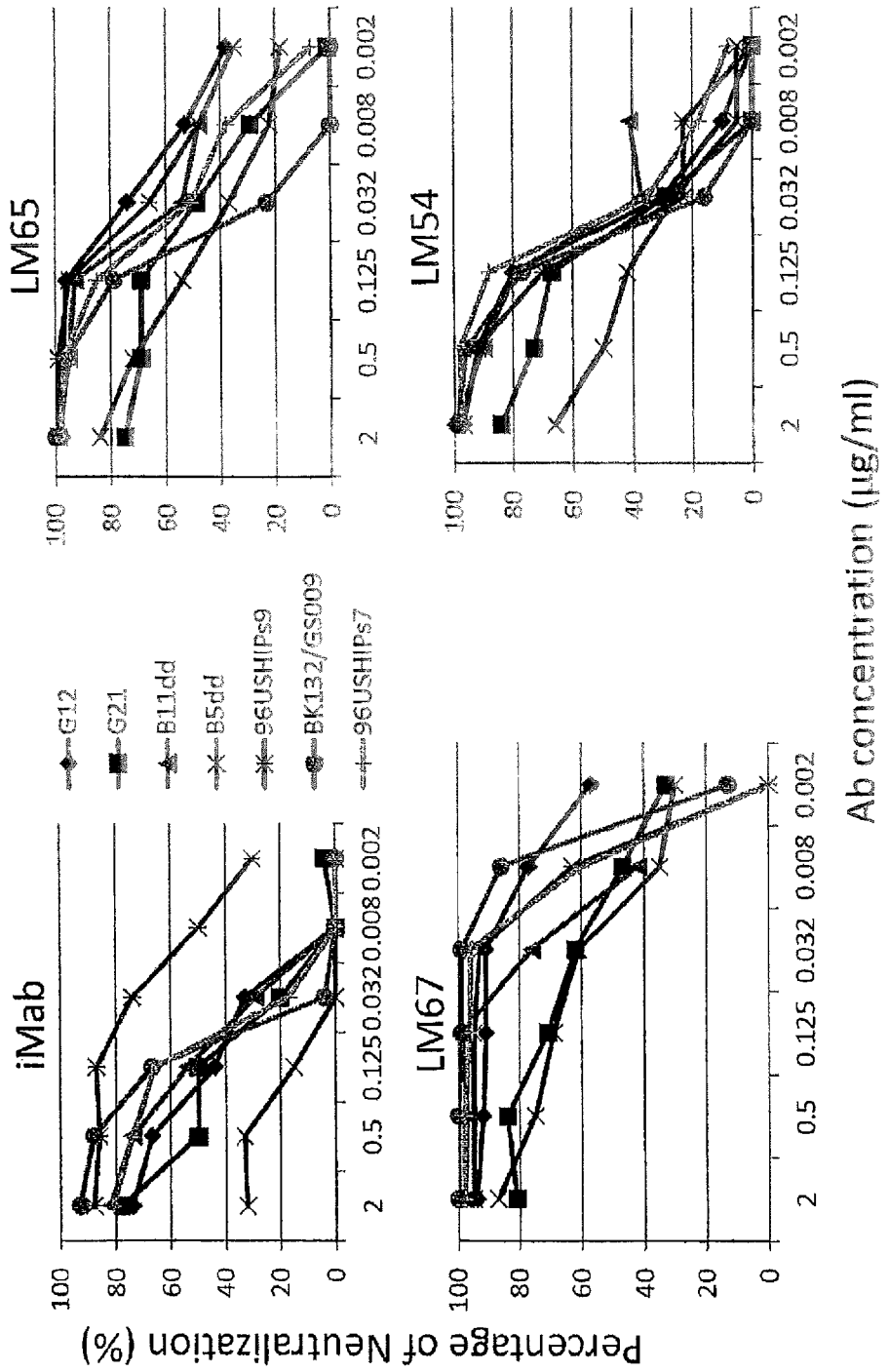
FIG. 6. A. LM30E, LM53, and LM52 enhanced the activity of iMab by neutralizing viruses otherwise resistant or partially resistant to wild type iMab. B. LM65, LM67, and LM54 also enhanced the activity of iMab. C. LM60 and LM76 did not enhance the activity of iMab.

V5 may allow a virus to bypass this steric hindrance and escape the anti-HIV activity of ibalizumab. The inventors hypothesized that addition of N-linked glycan sites onto ibalizumab at a region that is close to the gp120 V5 (for example near the N-terminus of V5) may allow the modified ibalizumab to neutralize viruses that are normally resistant to ibalizumab. The following experiments were conducted to test this hypothesis.

normally resistant or partially resistant to wild-type ibalizumab. Three other mutant ibalizumab antibodies (LM54, LM65, and LM67) also enhanced the neutralization activity of ibalizumab against resistant or partially resistant viruses (FIG. 6B). Two of the mutant ibalizumab antibodies, LM60 and LM76, did not enhance the neutralization activity of ibalizumab against resistant or partially resistant viruses (FIG. 6C).

TABLE 2

|  | WT | LM30E | LM52 | LM53 | LM54 | LM65 | LM67 | LM60 | LM76 |
| --- | --- | --- | --- | --- | --- | --- | --- | --- | --- |
| Ave MPI (%) | 75 | 98 | 98 | 99 | 93 | 93 | 91 | 75 | 78 |
| Distance (Å) |  | 14.9 | 13.5 | 14.1 | 15.5 | 16.1 | 18.6 | 19.6 | 23.4 |
| $IC_{80}$ (µg/ml) | 0.87 | 0.135 | 0.05 | 0.09 | 0.28 | 0.2 | 0.05 | 1.5 | 0.75 |

Locations in the Light Chain of iMab for Introducing N-Linked Glycan Site(s)

Figure 4B:
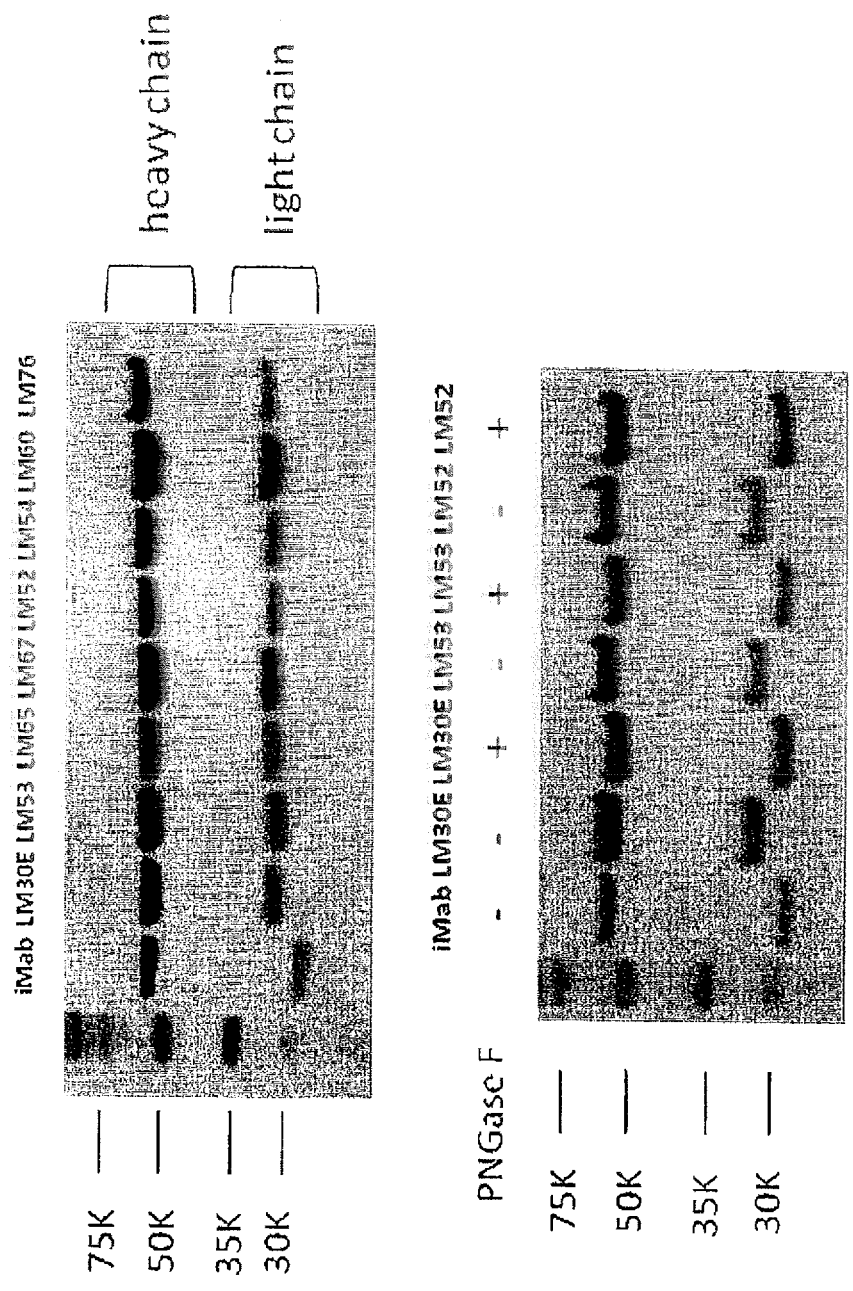
FIG. 4. A. The crystal structure of the ibalizumab-CD4 complex is depicted, showing several sites in the light chain of ibalizumab which were mutated to introduce an N-linked glycosylation site based on their close distance to the V5 of gp120. B. Expression and purification of iMab light chain mutants (LM). Increased mass in light chain observed relative to unmodified iMab was due to introduction of glycosylation site.

Based on the crystal structure of the ibalizumab-CD4 complex, several sites in the light chain of ibalizumab were selected based on their putatively close distance to the V5 of gp120. These include amino acid positions 30E, 67, 65, 52, 53, 54, 60, and 76—the numbering is based on the mature version of the light chain absent the 19 amino acid signal sequence and following the Kabat and Chothia Numbering Scheme which accounts for amino acid residues not accounted for in the original numbering. For example, position "30E" refers to the $5^{th}$ amino acid in a stretch of amino acids (30A, 30B, 30C, 30D, 30E, . . . ) between the positions originally numbered as 30 and 31. Potential N-linked glycosylation sites were introduced at each of these positions (FIG. 4A). As shown in FIG. 4B, the mutant light chains all had higher molecular weights than the wild type light chain (top panel), suggesting the presence of an added glycan in these mutants. When the mutant light chains were treated with the deglycosylation agent, PNGase F (bottom panel), their molecular weights dropped to that of a normal ibalizumab wild type light chain. These data confirmed that N-linked glycosylation sites were indeed added to the mutant light chains.

CD4 binding affinities of these mutant antibodies were examined using surface plasmon resonance. As shown in Table 1, these mutant ibalizumab antibodies all have binding affinities to CD4 protein comparable with the wild-type ibalizumab.

TABLE 1

| Antibody | Ka ($10^5$) | Kd ($10^{-5}$) | KD ($10^{-10}$) | Analyte |
| --- | --- | --- | --- | --- |
| ibalizumab wt | 2.8 | 12 | 4.3 | sCD4 |
| LM30E | 1.1 | 15 | 13 | sCD4 |
| LM53 | 2.9 | 13 | 5.3 | sCD4 |
| LM65 | 3.3 | 49 | 15 | sCD4 |
| LM67 | 2.5 | 20 | 8 | sCD4 |
| LM52 | 4.6 | 16 | 3.5 | sCD4 |
| LM54 | 3.7 | 27 | 4.5 | sCD4 |
| LM60 | 4.4 | 8.3 | 1.9 | sCD4 |
| LM76 | 5.0 | 14 | 2.8 | sCD4 |

Figure 5:
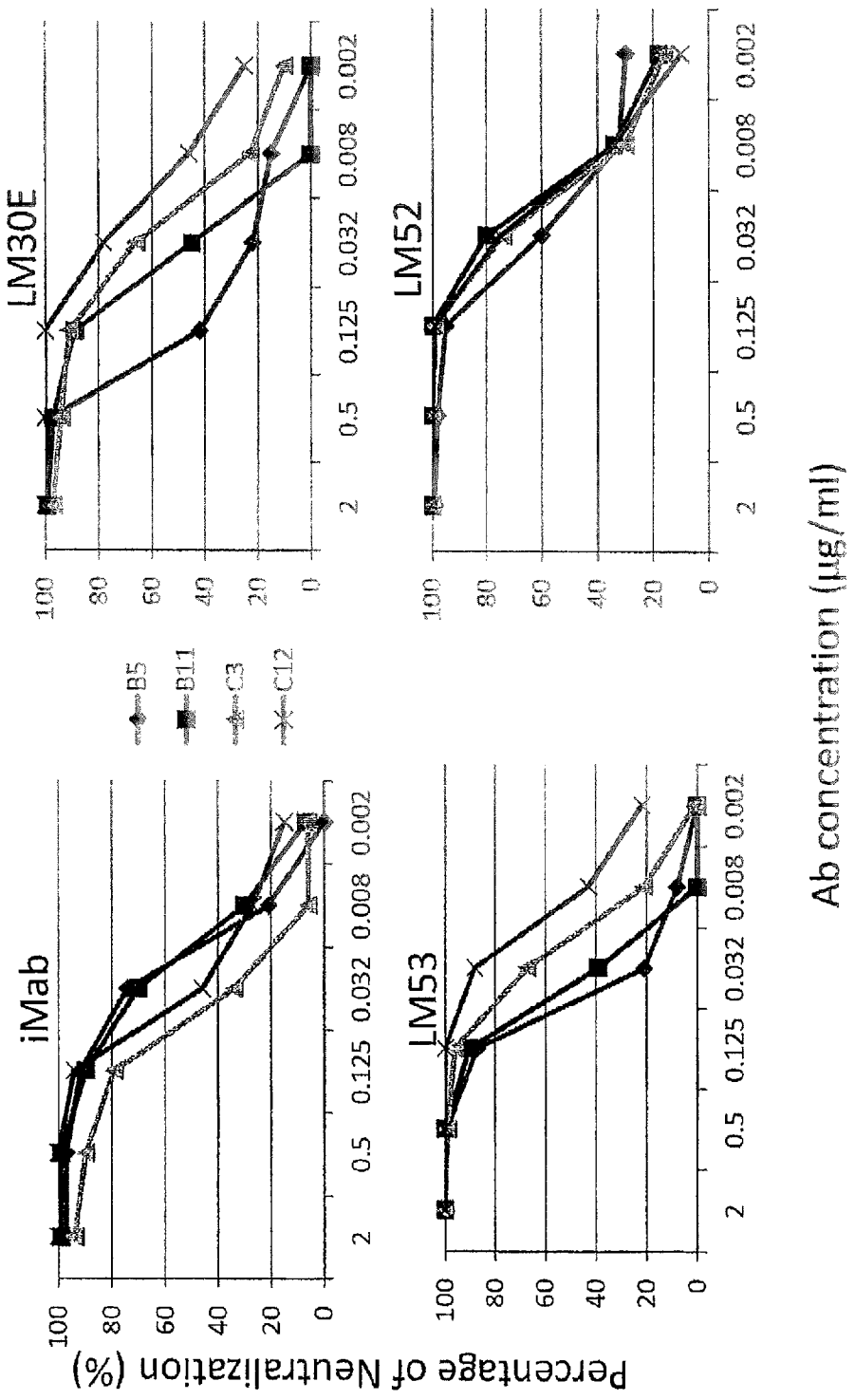
FIG. 5. iMab light chain glycan mutants of iMab can neutralize iMab-sensitive viruses.

The mutant ibalizumab antibodies were also tested in neutralization assays against a number of viral isolates. FIG. 5 depicts the neutralization activities of LM30E, LM53 and LM52 mutants, similar to the neutralization activities of wild type iMab, against viral isolates B5, B11, C3 and C12. Notably, as shown in FIG. 6A, three of the mutant ibalizumab antibodies (LM30E, LM52, and LM53) greatly enhanced neutralization activity against viruses that are Based on modeling utilizing the ibalizumab-CD4 and CD4-gp120 crystal structures, the three ibalizumab light chain glycan mutants having the best neutralization breadth also had glycosylation sites closest to the V5 loop of gp120, as shown in Table 2. The two mutants that did not improve neutralization breadth had glycosylation sites that are further away from V5. LM52 had the best overall activity among all mutants.

Size of Glycan Introduced

Figure 7B:
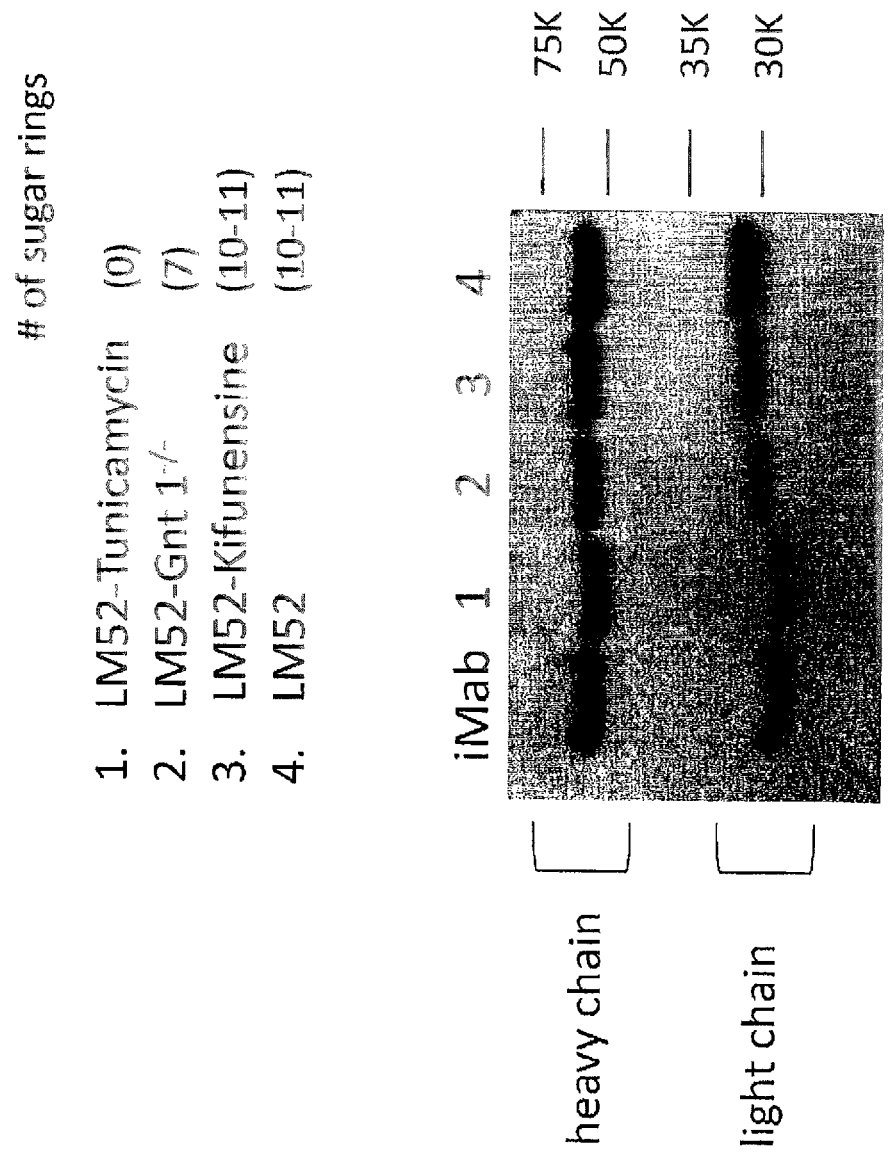
Figure 7C:
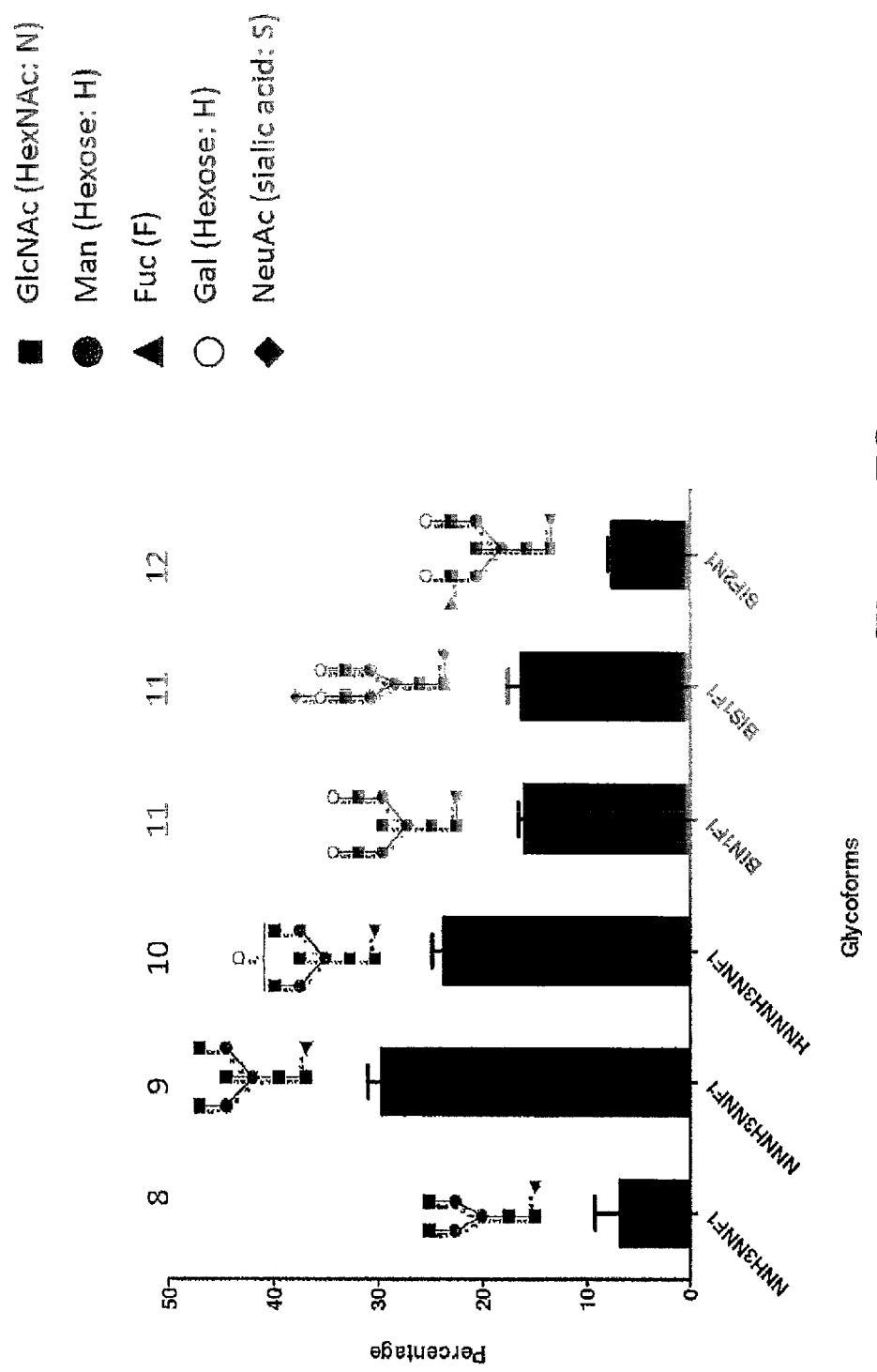
Figure 7D:
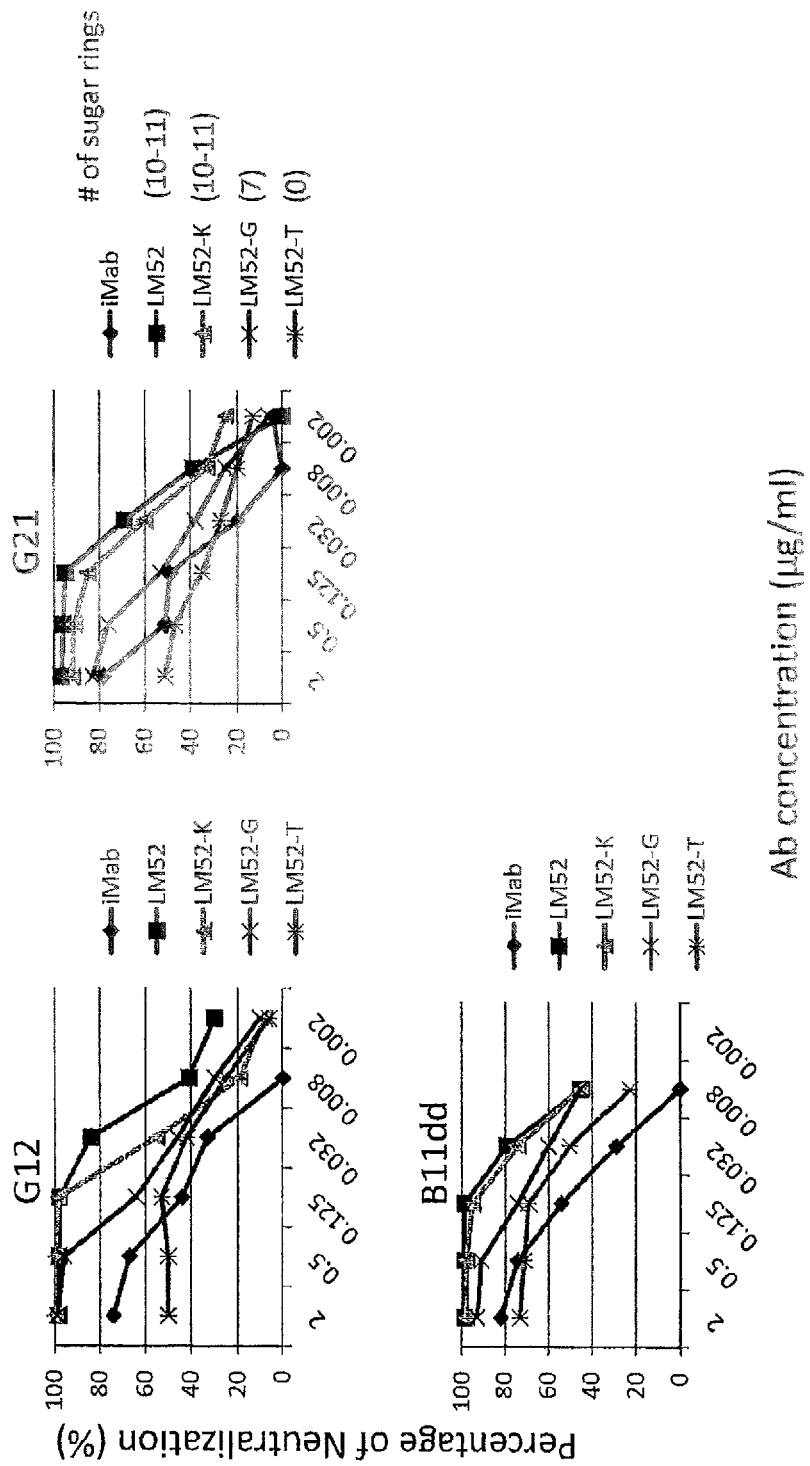

To determine whether the size of glycan would affect the ability of the light chain mutants to enhance the breadth of ibalizumab, a panel of inhibitors and cell lines were utilized to exploit the natural cellular glycosylation pathway (FIG. 7A) in order to generate variations of one ibalizumab light chain mutant (LM52) with glycans of different sizes (FIG. 7B). The constituents of the resulting N-glycans in LM52 were determined by mass spectrometry, which revealed that most of the glycans had 9-12 rings (FIG. 7C). The LM52 mutants, differing only in their glycan sizes, were tested in neutralization assays. Higher neutralization activities were observed with LM52 mutant proteins with bigger N-linked glycans in all of the three viruses tested (FIG. 7D).

Different Cell Lines

Figure 8A:
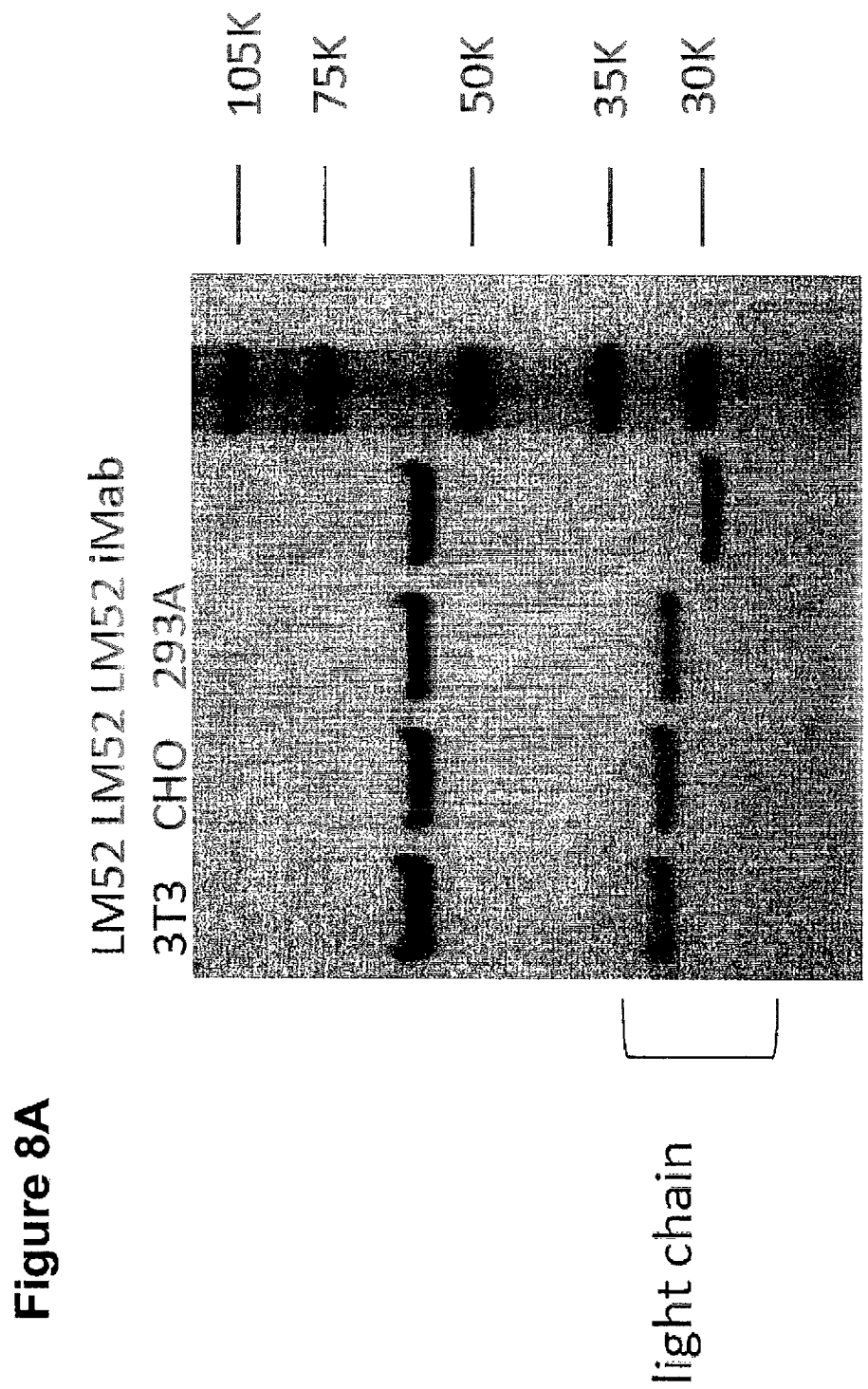
FIG. 8. LM52 mutant produced in different cell lines was shown to have glycans of similar sizes (A) and neutralization activities (B).
Figure 8B:
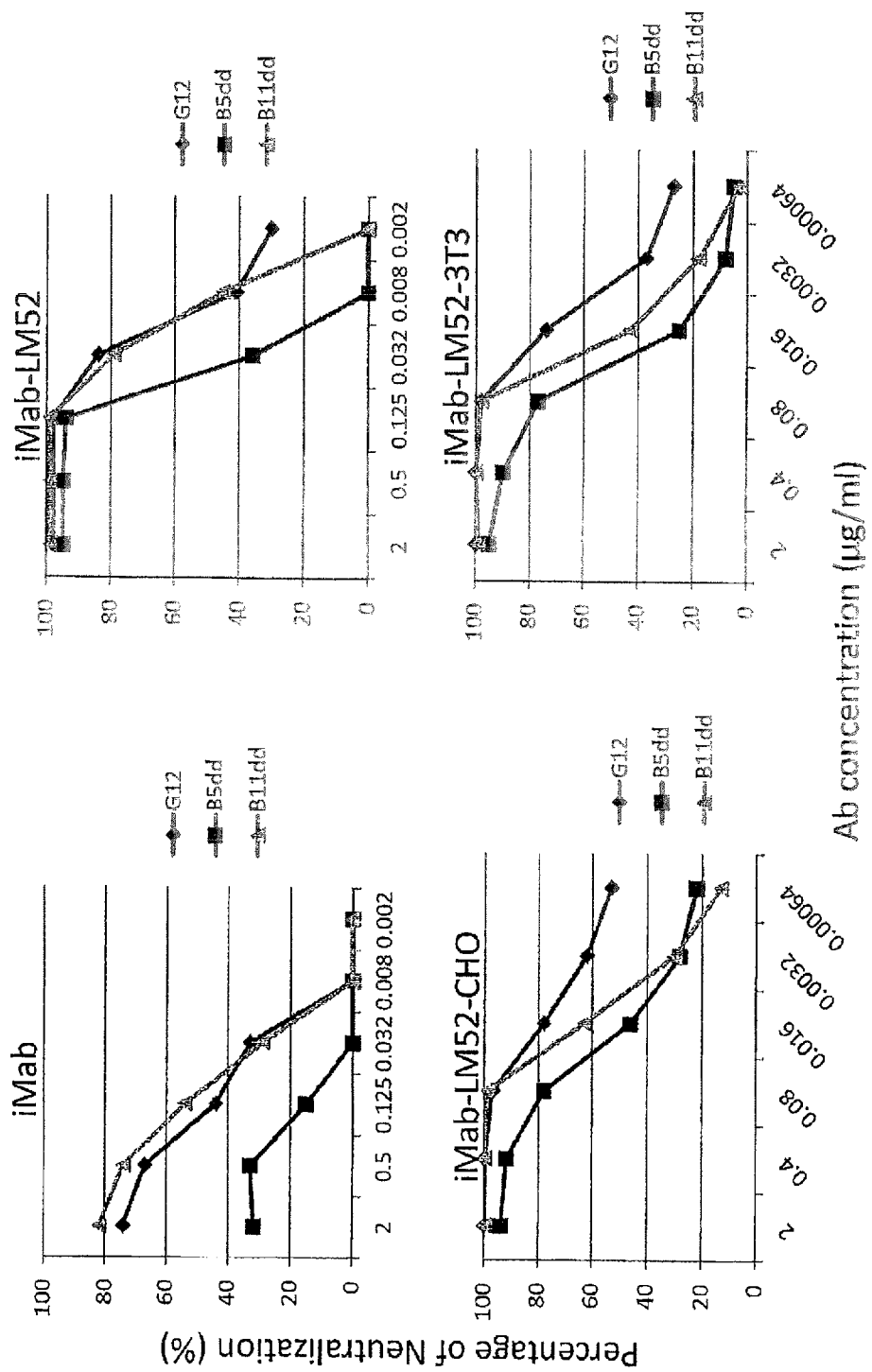

The inventors also evaluated whether the activity of LM52 would be similar if this mutant ibalizumab was produced in different mammalian cell lines. Three cell lines were used: 3T3, CHO and 293A. The sizes of the light chain produced from these cell lines were similar (FIG. 8A). The functional activities of iMab-LM52 produced in different cell lines were also similar and all manifested an improved breadth of HIV neutralization activity as compared to wild type ibalizumab (FIG. 8B).

Breadth and Potency of iMab-LM52 Against a Multiple-Clade Panel of Viruses

As shown in FIG. 9A, Ibalizumab LM52 significantly improved the breadth of ibalizumab as determined by maximum percent inhibition against a 118 Env-psuedotyped cross-clade panel. LM52 can neutralize 100% of these viruses by at least 80% at a concentration even lower than 1 ug/ml, demonstrating its exquisite potency (FIG. 9B). Based on the comparison of iMab-LM52 to other broad potent HIV neutralizing antibodies (Table 3), Ibalizumab LM52 is the broadest and most potent monoclonal antibody against HIV-1 entry evaluated to date.

TABLE 3

| Abs | | VRC01 | PG9 | 3BNC117 | PGT121 | PGT128 | NIH45-46G54W | iMab | iMab-52 |
|---|---|---|---|---|---|---|---|---|---|
| IC50 (ug/ml) | Breadth (%) | 88 | 86 | 89 | 70 | 72 | 88 | 92 | 100 |
| | Geometric mean | 0.45 | 1.27 | 0.24 | 0.53 | 0.39 | 0.04 | 0.074 | 0.014 |
| | Arithmetic mean | 4.41 | 15.89 | 6.36 | 16.63 | 15.31 | 5.26 | 1.02 | 0.016 |
| | Median | 0.34 | 0.62 | 0.13 | 0.31 | 0.1 | 0.03 | 0.04 | 0.015 |

Breadth: IC50 < 50 ug/ml (while iMab and iMab-52 was tested at 10 ug/ml)

The results from the above experiments indicate that the addition of N-linked glycans in the light chain of iMab leads to significantly improved breadth in its neutralization activity. The closer the glycosylation site on iMab light chain is to gp120 V5, the better activity the mutant has, with LM30E, LM53, and LM52 mutants all showing greatly enhanced breadth compared to wild type iMab. Further, mutants having glycans bigger than 7-rings at position 52 enhanced iMab breadth, with bigger glycans conferring better activities. This is the first example of improving the function of a mAb through glycan modification in the variable region.

```
                          Sequence Listing

SEQ ID NO: 1-Amino acid sequence of the human CD4 receptor (amino acids 1-25
representing a signal peptide, amino acids 26-122 constituting D1, and amino
acids 123-205 constituting D2):

MNRGVPFRHLLLVLQLALLPAATQGKKVVLGKKGDTVELTCTASQKKSIQFHWKNSNQIKILGNQGSFLTKGPSKL
NDRADSRRSLWDQGNFPLIIKNLKIEDSDTYICEVEDQKEEVQLLVFGLTANSDTHLLQGQSLTLTLESPPGSSPSVQCRS
PRGKNIQGGKTLSVSQLELQDSGTWTCTVLQNQKKVEFKIDIVVLAFQKASSIVYKKEGEQVEFSFPLAFTVEKLTGSGEL
WWQAERASSSKSWITFDLKNKEVSVKRVTQDPKLQMGKKLPLHLTLPQALPQYAGSGNLTLALEAKTGKLHQEVNLV
VMRATQLQKNLTCEVWGPTSPKLMLSLKLENKEAKVSKREKAVWVLNPEAGMWQCLLSDSGQVLLESNIKVLPTWST
PVQPMALIVLGGVAGLLLFIGLGIFFCVRCRHRRRQAERMSQIKRLLSEKKTCQCPHRFQKTCSPI

SEQ ID NO: 2-Amino acid sequence of the heavy chain of iMab MV1 (471 amino acids,
including the first 19 amino acid residues constituting a leader sequence)

MEWSGVPMFLLSVTAGVHSQVQLQQSGPEVVKPGASVKMSCKASGYTFTSYVIHWVRQKPGQGLDWIGYINPY
NDGTDYDEKFKGKATLTSDTSTSTAYMELSSLRSEDTAVYYCAREKDNYATGAWFAYWGQGTLVTVSSASTKGPSVFPL
APSSKSTSGGTAALGCLVKDYFPEPVTVSWNSGALTSGVHTFPAVLQSSGLYSLSSVVTVPSSSLGTQTYICNVNHKPSN
TKVDKKVEPKSCDKTHTCPPCPAPEFEGGPSVFLFPPKPKDTLMISRTPEVTCVVVDVSHEDPEVKFNWYVDGVEVHN
AKTKPREEQYNSTYRVVSVLTVLHQDWLNGKEYKCKVSNKALPASIEKTISKAKGQPREPQVYTLPPSRDELTKNQVSLT
CLVKGFYPSDIAVEWESNGQPENNYKTTPPVLDSDGSFFLYSKLTVDKSRWQQGNVFSCSVMHEALHNHYTQKSLSLS
PGK*

SEQ ID NO: 3-Amino acid sequence of the light chain of iMab MV1 (238 amino acids,
including the first 19 amino acids which constitute a leader sequence)

MEWSGVFIFL  LSVTAGVHSD  IVMTQSPDSL  AVSLGERVTM  NCKSSQSLLY  STNQKNYLAW
YQQKPGQSPK  LLIYWASTRE  SGVPDRFSGS  GSGTDFTLTI  SSVQAEDVAV  YYCQQYYSYR
TFGGGTKLEI  KRTVAAPSVF  IFPPSDEQLK  SGTASVVCLL  NNFYPREAKV  QWKVDNALQS
GNSQESVTEQ  DSKDSTYSLS  STLTLSKADY  EKHKVYACEV  THQGLSSPVT  KSFNRGEC

SEQ ID NO: 4 (LM52)
DIVMTQSPDSLAVSLGERVTMNCKSSQSLLYSTNQKNYLAWYQQKPGQSPKLLIYWANSTESGVPDRFSG
SGSGTDFTLTISSVQAEDVAVYYCQQYYSYRTFGGGTKLEIKRTVAAPSVFIFPPSDEQLKSGTASVVCL
LNNFYPREAKVQWKVDNALQSGNSQESVTEQDSKDSTYSLSSTLTLSKADYEKHKVYACEVTHQGLSSPV
TKSFNRGEC

The underlined amino acids represent "30E Gln", "52Ser", "53Thr", "54Arg", "60Asp", "65Ser",
"67Ser", and "76Ser". The amino acid changes made to the sequence in order to introduce a new
N-linked glycosylation site at each of these positions are:
30E Gln, 31Lys, 32Asn changed to 30E Asn, 31Ala, 32Thr
52Ser, 53Thr, 54Arg changed to 52Asn, 53Ser, 54Thr
53Thr, 54Arg, 55Glu changed to 53Asn, 54Ala, 55Thr
54Arg, 55Glu, 56Ser changed to 54Asn, 55Ala, 56Thr
60Asp, 61Arg, 62Phe changed to 60Asn, 61Ala, 62Thr
65Ser, 66Gly, 67Ser changed to 65Asn, 66Ala, 67Thr
67Ser, 68Gly, 69Thr changed to 67Asn, 68Ala, 69Thr
76Ser, 77Ser, 78Val changed to 76Asn, 77Ala, 78Thr
```

What is claimed is:

1. An anti-CD4 antibody comprising a heavy chain comprising the amino acid sequence of SEQ ID NO: 2 and a light chain comprising the amino acid sequence of SEQ ID NO: 4.

2. A pharmaceutical composition comprising the antibody of claim 1 and at least one pharmaceutically acceptable carrier.

* * * * *

UNITED STATES PATENT AND TRADEMARK OFFICE
CERTIFICATE OF CORRECTION

PATENT NO.        : 9,587,022 B2  
APPLICATION NO.   : 14/133256  
DATED             : March 7, 2017  
INVENTOR(S)       : Ruijiang Song et al.

Page 1 of 1

It is certified that error appears in the above-identified patent and that said Letters Patent is hereby corrected as shown below:

In the Claims

Claim 1, Column 23, Line 59, replace "An anti-CD4 antibody" with --An anti-CD4 monoclonal antibody--.

Signed and Sealed this  
Eleventh Day of July, 2017

Joseph Matal  
*Performing the Functions and Duties of the*  
*Under Secretary of Commerce for Intellectual Property and*  
*Director of the United States Patent and Trademark Office*